United States Patent [19]

Branch et al.

[11] Patent Number: 4,835,150

[45] Date of Patent: May 30, 1989

[54] CEPHEM COMPOUNDS

[75] Inventors: Clive L. Branch, Dorking; Arun C. Kaura, Horsham, both of England

[73] Assignee: Beecham Group p.l.c., England

[21] Appl. No.: 877,295

[22] Filed: Jun. 23, 1986

[30] Foreign Application Priority Data

Jun. 25, 1985 [GB] United Kingdom ............... 8516020
Dec. 23, 1985 [GB] United Kingdom ............... 8531681

[51] Int. Cl.$^4$ .................. C07D 501/57; A61K 31/545
[52] U.S. Cl. .................................. 514/201; 540/221
[58] Field of Search ............... 540/222, 221, 227; 514/201

[56] References Cited

U.S. PATENT DOCUMENTS 4,539,149  9/1985  Milnes ............................... 540/221

FOREIGN PATENT DOCUMENTS 0071395  2/1983  European Pat. Off.

Primary Examiner—Nicholas S. Rizzo
Attorney, Agent, or Firm—Jacobs & Jacobs

[57] ABSTRACT

β-Lactam antibiotics are disclosed which have the formula (IA) or pharmaceutically acceptable salts or pharmaceutically acceptable in vivo hydrolyzable esters thereof:

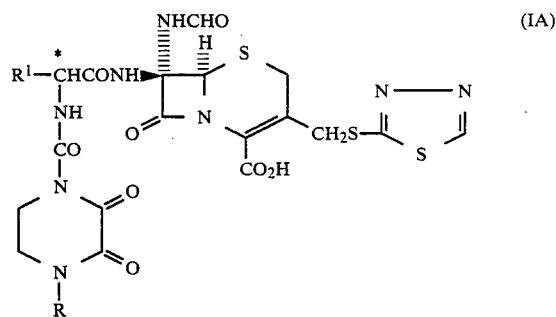

wherein $R_1$ is phenyl, 3-hydroxyphenyl, 4-hydroxyphenyl, 3-aminophenyl, 4-aminophenyl, or 3,4-dihydroxyphenyl, the hydroxy and amino groups being optionally protected, and R is $C_{1-8}$ alkyl; and also the use thereof.

Processes for the preparation of the compounds are disclosed together with intermediates for use therein.

10 Claims, No Drawings

CEPHEM COMPOUNDS

This invention relates to a class of novel β-lactam derivatives, which have antibacterial activity and are of value in the treatment of infections in animals especially mammals including man caused by a wide range of organisms, particularly Gram-negative organisms. The invention also relates to a process for the preparation of such compounds, intermediates for use in the preparation of the compounds and to pharmaceutical compositions comprising the antibacterially active compounds European Patent Application No. 82303821.1 (Publication No. 0 071 395) discloses a class of β-lactam antibiotics having an α-formamido (formamidyl) substituent on the carbon atom adjacent to the carbonyl group of the β-lactam ring.

It has now been found that, within this class of compounds, there exist cephalosporin derivatives with outstanding antibacterial properties.

Accordingly the present invention provides a compound of formula (I) or a salt thereof:

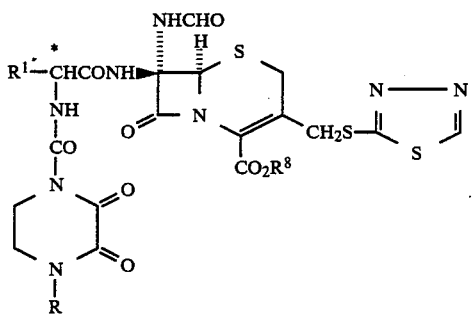

wherein $R^1$ is phenyl, 3-hydroxyphenyl, 4-hydroxyphenyl, 3-aminophenyl, 4-aminophenyl, or 3,4-dihydroxyphenyl, the hydroxy and amino groups being optionally protected; R is $C_{1-8}$ alkyl; and $R^8$ is hydrogen or a readily removable carboxy protecting group.

The optional protecting groups for the hydroxy or amino groups attached to the phenyl ring in $R^1$ are suitably readily cleaved and include in vivo hydrolysable groups as well as groups which may be cleaved by conventional chemical or enzymatic methods.

A comprehensive discussion of the ways in which hydroxy and amino groups may be protected and methods for cleaving the resulting protected derivatives are given, for example, in "Protective Groups in Organic Synthesis" by T. W. Greene (Wiley-Interscience, New York, 1981). Particularly suitable protecting groups include those which, when protecting the 3- and/or 4-hydroxy group in $R^1$ afford esters or carbonates (both of which may be in vivo hydrolysable), ethers (including silyl ethers) and ketals (for example tetrahydropyranyloxy derivatives, sometimes described as 'THP ethers'). When $R^1$ is 3- or 4-aminophenyl, suitable protecting groups include, for example, those that afford amides and carbamates.

When $R^1$ is 3,4-dihydroxyphenyl it will be understood that one or both of the hydroxy groups may be protected. When both hydroxy groups are protected it will be understood that a different protecting group may be used for each hydroxy group, although, more conveniently, the protecting groups used will be the same.

Examples of suitable protecting groups for the 3- and/or 4-hydroxy group in $R^1$ include formyl and optionally substituted $C_{1-6}$ alkylcarbonyl and arylcarbonyl groups such as acetyl, chloroacetyl, dichloroacetyl and benzoyl; optionally substituted $C_{1-6}$ alkoxycarbonyl and aryl $C_{1-6}$ alkoxycarbonyl, for example ethoxycarbonyl, trimethylsilylethoxycarbonyl, benzyloxycarbonyl and 4-nitrobenzyloxycarbonyl; and optionally substituted $C_{2-6}$ alkenyloxycarbonyl such as allyloxycarbonyl.

Further examples of suitable protecting groups for the 3- and/or 4-hydroxy group in $R^1$ include aryl, aryl $C_{1-6}$ alkyl, optionally substituted $C_{1-6}$ alkyl, optionally substituted $C_{2-6}$ alkenyl, optionally substituted $C_{3-7}$ cycloalkyl, and silyl groups.

Some examples of optional substituents in protecting groups mentioned hereinabove as being optionally substituted include up to three groups (which may be the same or different) chosen from halogen, hydroxy, $C_{1-6}$ alkoxy, $C_{1-6}$ alkylthio, cyano, nitro, carboxy, carboxylic acid $C_{1-6}$ akyl ester, carbamoyl, amino, mono $(C_{1-6})$ alkylamino, and di $(C_{1-6})$ alkylamino.

Preferred alkyl protecting groups for the 3- and/or 4-hydroxy group in $R^1$ include, for example, methyl or ethyl, optionally substituted with $(C_{1-6})$ alkoxy or $(C_{1-6})$ alkylthio, for example with methoxy, ethoxy, or methylthio. Further useful protecting groups are methoxyethoxymethyl and (trimethylsilyl) ethoxymethyl. In addition, when $R^1$ is 3,4-dihydroxyphenyl, the hydroxy groups may be protected by an alkylene bridge so that $R^1$ becomes, for example, 3,4-[1,1-dimethyl(methylenedioxy)]phenyl.

Preferred aryl $C_{1-6}$ alkyl protecting groups for the 3-and/or 4-hydroxy group in $R^1$ include benzyl and 4-nitrobenzyl.

Preferred silyl protecting groups may be substituted with $C_{1-6}$ alkyl and/or phenyl groups and include, for example, trimethylsilyl, t-butyldimethylsilyl, t-butyldiphenylsilyl, triethylsilyl, isopropyldimethylsilyl, triphenylmethyldimethylsilyl and the like. The resulting silyl ethers may be cleaved by methods known in the art, such as those described by T. W. Greene (loc. cit.) or by M. Lalonde and T. H. Chan in *Synthesis*, 1985 (September), pages 817-845 and references therein.

Particularly preferred hydroxy protecting groups are acetyl and trimethylsilyl.

From the foregoing it may be seen that in one favoured group of compounds according to the invention $R^1$ is phenyl, 3-hydroxyphenyl, 3-tri($C_{1-6}$ alkyl)silyloxyphenyl, 3-($C_{1-6}$ alkylcarbonyloxy)phenyl, 3-($C_{1-6}$ alkyloxycarbonyloxy)phenyl, 3-(benzyloxycarbonyloxy)phenyl, 3-(4-nitrobenzyloxycarbonyloxy)phenyl, 3-aminophenyl, 4-hydroxyphenyl, 4-tri($C_{1-6}$ alkyl)silyloxyphenyl 4-($C_{1-6}$ alkylcarbonyloxy)phenyl, 4-($C_{1-6}$ alkyloxycarbonyloxy)phenyl, 4-(benzyloxycarbonyloxy)phenyl, 4-(4-nitrobenzyloxycarbonyloxy)phenyl, 4-aminophenyl 3,4-dihydroxyphenyl, 3,4-bis[tri($C_{1-6}$ alkyl)silyloxy]phenyl 3,4-di ($C_{1-6}$ alkyloxycarbonyloxy)phenyl, 3,4-di-(benzyloxycarbonyloxy)phenyl, or 3,4-di-(4-nitrobenzyloxycarbonyloxy)phenyl.

Preferred groups for $R^1$ are 3,4-dihydroxyphenyl, 3,4-diacetoxyphenyl, 4-hydroxyphenyl, 3-hydroxyphenyl, 3-acetoxyphenyl, and 4-acetoxyphenyl.

A particularly preferred group for $R^1$ is 3,4-dihydroxyphenyl.

In formula (I), the group R is $C_{1-8}$ alkyl. More suitably it is $C_{1-6}$ alkyl, preferably $C_{1-4}$ alkyl.

A particularly preferred group for R is ethyl.

The carbon atom marked * in formulae herein is asymmetric and thus compounds of formula (I) may exist as two optically active diastereoisomers. In general the isomer prepared from the D-side chain exhibits the highest antibacterial activity and accordingly the D compound or the DL mixtures are preferred, with the D compound being particularly preferred.

The compounds of formula (I) with the preferred D-side-chain can be separated from a mixture of both diastereoisomers by conventional methods, or prepared from intermediates that bear a D- side chain.

The formamido group can exist in two preferred conformations, i.e. those wherein the hydrogen atoms of the -NH-CHO are cis- or trans-, of which the cis conformation normally predominates.

Non-pharmaceutically acceptable salts of the compound of formula (I) wherein $R^8$ is hydrogen are primarily of use as intermediates in the preparation of a compound of formula (I) wherein $R^8$ is hydrogen or a pharmaceutically acceptable salt thereof. Salts within compounds of formula (I) may be prepared by salt exchange in conventional manner.

Similarly, carboxy-protected derivatives of formula (I), i.e. those compounds of formula (I) wherein $R^8$ is a readily removable carboxy protecting group, may be used as intermediates in the preparation of a compound of the formula (I) wherein $R^8$ is hydrogen, or a pharmaceutically acceptable salt thereof. Included within the scope of readily removable carboxy protecting groups for $R^8$ are carboxy protecting groups $R^x$ as defined hereinafter and pharmaceutically acceptable in vivo hydrolysable ester groups.

Since the β-lactam antibiotic compounds of the present invention are intended for use in pharmaceutical compositions, it will be readily appreciated that preferred compounds within formula (I) are pharmaceutically acceptable, i.e. are compounds of formula (IA) or pharmaceutically acceptable salts or pharmaceutically acceptable in vivo hydrolysable esters thereof:

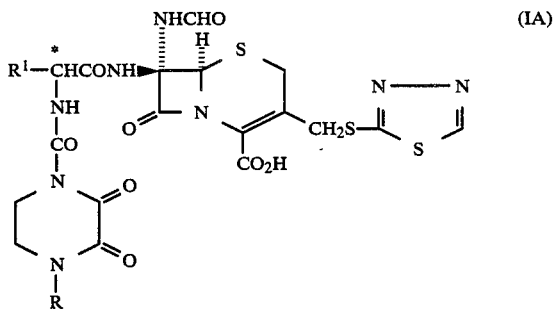

wherein $R^1$ and R are as defined with respect to formula (I).

It will be further understood that the β-lactam antibiotic compounds of the present invention are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical it will readily be understood that the substantially pure form is preferred as for the β-lactam antibiotic compounds.

Preferably, whenever possible, the compounds of the present invention are obtained in crystalline form.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

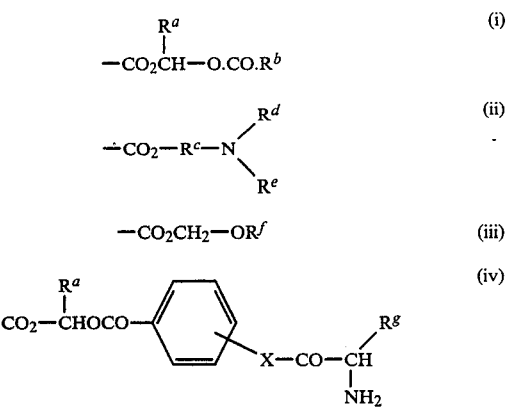

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is oxygen or NH.

Examples of suitable pharmaceutically acceptable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

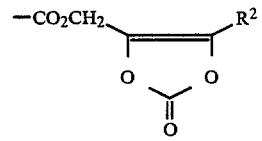

wherein $R^2$ is hydrogen, $C_{1-6}$ alkyl or phenyl.

Suitable pharmaceutically acceptable salts of the carboxy group of the compound of formula (I) include metal salts, eg aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)-amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-$\beta$- phenethylamine, dehydroabietylamine, N,N'-bisdehydro-abietylamine, ethylenediamine, or bases of the pyridine type such as pyridine, collidine or quinoline, or other amines which have been used to form salts with known penicillins and cephalosporins. Other useful salts include the lithium salt and silver salt.

Some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Specific compounds within this invention include the following and pharmaceutically acceptable salts and in-vivo hydrolysable esters thereof:

7$\beta$-[D-2-(3,4-Diacetoxyphenyl)-2-[(4-ethyl-2,3-dioxopiperazin-1-yl)carbonylamino]acetamido]-7$\alpha$-formamido-3-[(1,3,4-thiadiazol-2-yl)thiomethyl]ceph-3-em-4-carboxylic acid.

7$\beta$-[D-2-(3,4-Dihydroxyphenyl)-2-[(4-ethyl-2,3-dioxopiperazin-1-yl)carbonylamino]acetamido]-7$\alpha$-formamido-3-[(1,3,4-thiadiazol-2-yl)thiomethyl]ceph-3-em-4carboxylic acid.

7$\beta$-[D-2-[(4-Ethyl-2,3-dioxopiperazin-1-yl)carbonylamino]-2-phenylacetamido]-7$\alpha$-formamido-3-[(1,3,4-thiadiazol-2-yl)thiomethyl]ceph-3-em-4-carboxylic acid.

7$\beta$-[D-2-(4-Acetoxyphenyl)-2-[(4-ethyl-2,3-dioxopiperazin-1-yl)carbonylamino]acetamido]-7$\alpha$-formamido-3-[(1,3,4-thiadiazol-2-yl)thiomethyl]ceph-3-em-4-carboxylic acid.

7$\beta$-[D-2-[(4-Ethyl-2,3-dioxopiperazin-1-yl)carbonylamino]-2-(4-hydroxyphenyl)acetamido]-7$\beta$-formamido-3-[(1,3,4-thiadiazol-2-yl)thiomethyl]ceph-3-em-4-carboxylic acid.

7$\beta$-[D,L-2-(3-Acetoxyphenyl)-2-[(4-ethyl-2,3-dioxopiperazin-1-yl)carbonylamino]acetamido]-7$\beta$-formamido-3-[(1,3,4-thiadiazol-2-yl)thiomethyl]ceph-3-em-4-carboxylic acid.

7$\beta$-[D,L-2-[(4-Ethyl-2,3-dioxopiperazin-1-yl)carbonylamino]-2-(3-hydroxyphenyl)acetamido]-7$\alpha$-formamido-3-[(1,3,4-thiadiazol-2-yl)thiomethyl]ceph-3-em-4-carboxylic acid.

7$\beta$-[D,L-2-(4-Aminophenyl)-2-[(4-ethyl-2,3-dioxopiperazin-1-yl)carbonylamino]acetamido]-7$\alpha$-formamido-3-[(1,2,4-thiadiazol-2-yl)thiomethyl]ceph-3-em-4-carboxylic acid.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a pharmaceutically acceptable compound of formula (IA) or a salt or in vivo hydrolysable ester thereof together with a pharmaceutically acceptable carrier or excipient.

The compositions may be formulated for administration by any suitable route, such as oral or parenteral, or by topical application. The compositions may be in the form of tablets, capsules, powders, granules, lozenges, creams or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with eater or other suitable vehicle before use. Such liquid preparations may contain conventional addtives such as suspending agents, for example sorbitol, methyl cellulose, glucose syrup, gelating, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository base, eg cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitble vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. the compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 mg to 12 g per day for an average adult patient (70 kg.), for instance 1500 mg per day, depending on the route and frequency of administration. Such dosages correspond to approximately 1.5 to 170 mg/kg per day. Suitable the dosage is from 1 to 6 g. per day.

The daily dosage is suitably given by administering a compound of the invention several times in a 24-hour period. Typically, 250 mg. is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a pharmaceutically acceptable compound of the invention of formula (IA) or a salt or in vivo hydrolysable ester thereof is administered in the above mentioned dosage range.

The antibiotic compounds according to the present invention may be the sole therapeutic agent in the compositions of the invention or a combination with other antibiotics and/or β-lactamase inhibitor may be employed.

Advantageusly the compositions also comprise a compound of formula (II) or a pharmaceutically acceptable salt or ester thereof:

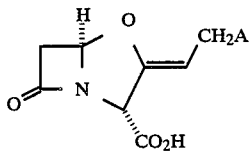
(II)

wherein A us hydroxyl; substituted hydroxyl; thiol; a group of formula $SO_2R^3$ wherein $R^3$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises a pharmaceutically acceptable antibiotic compound of the formula (IA) or a salt or in vivo hydrolysable ester thereof and a pharmaceutically acceptable carrier or excipient together with a β-lactamase inhibitor of formula (III) or a pharmaceutically acceptable salt or in vivo hydrolyssable ester thereof:

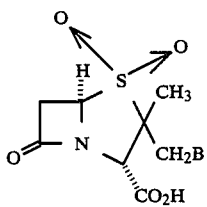
(III)

wherein B is hydrogen, halogen or a groups of formula:

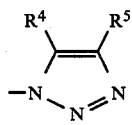

in which $R^4$ and $R^5$ are the same or different and each is hydrogen, $C_{1-6}$ alkoxycarbonyl, or carboxy or a pharmaceutically acceptable salt thereof.

Further suitable β-lactamase inhibitors include 6-alkylidene penems as described in European Patent Application No. 81301683.9 (Publication No. 0 041 768).

Further suitable β-lactamase inhibitors include 6β-bromopenicillanic acid and salts and in vivo hydrolysable esters therof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of a pharmaceutically acceptable antibiotic compound of this invention of the formula (IA) or a salt or in vivo hydrolysable ester thereof.

The pharmaceutically acceptable antibiotic compounds of the present invention of formula (IA) or salt or in vivo hydrolysable esters thereof are active against a broad range of gram positive and Gram negative bacteria, and may be used to treat a wide range of bacterial infections including those in immunocompromised patients.

Amongst many other uses, the pharmaceutically acceptable compounds of the invention of formula (IA) or salts or in vivo hydrolysable esters thereof are of value in the treatment of respiratory tract and urinary tract infections in humans and may also be used to treat mastitis in cattle. A particular advantage of the antibacterially active compounds of this invention is their stability to β-lactamase enzymes and they are therefore effective against β-lactamase producing organisms.

The present invention further provides a process for the preparation of a compound of formula (I) which process comprises treating a compound of formula (IV):

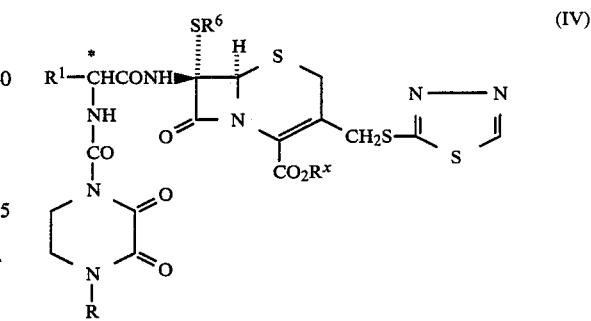
(IV)

wherein R, $R^1$ and * are as hereinbefore defined and wherein any reactive groups may be protected; $R^x$ is a readily removable carboxy protecting groups; and $R^6$ is $C_{1-6}$ alkyl, aryl or benzyl; with a heavy metal ion such as mercury, silver, thallium, lead or copper; and thereafter in situ with a nucleophilic derivative of formamide as described in European Patent Appliction No. 84300338.5 (Publication No. 0 115 405).

At the end of the process described hereinabove and in other processes for the preparation of the compound of formula (I) described hereinbelow it may be necessary ro remove protecting groups. Deprotection may be carried out by any convenient method known in the art that does not cause unwanted side reactions to occur to any appreciable extent. Methods that are particularly suitable for converting an acetoxy group in $R^1$ into a hydroxy group include treatment with aqueous sodium sulphite solution or aqueous sodium hydrogen carbonate solution, or treatment with an esterase, especially citrus acetylesterase. When a ydroxy group in $R^1$ is protected as a silyl ether, for example the trimethylsily ether, removal of the silyl group is normally carried out by acid hydrolysis.

In an alternative aspect, the present invention provides a process for the preparation of a compound of formula (I) which process comprises treating a compound of formula (IVA):

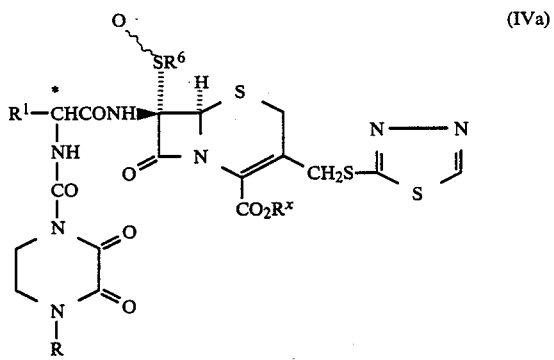

wherein R, $R^1$, *, $R^X$, and $R^6$ are as defined for formula (IV) and wherein any reactive groups may be protected; with a nucleophilic derivative of formamide; and thereafter, if necessary, carrying out one or more of the following steps:

(i) converting the group $R^X$ into a group $R^8$;
(ii) removing any protecting groups on $R^1$; and
(iii) converting the product to a salt.

The present invention further provides a process for the preparation of a compound of formula (I) which process comprises formylating a compound of formula (V):

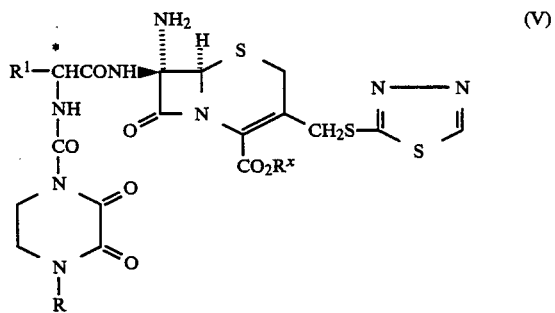

wherein R, $R^1$, $R^X$ and * are as hereinbefore defined and wherein any reactive groups may be protected; and thereafter, if necessary, carrying out one or more of the following steps:

(i) converting the group $R^X$ into a group R'1 8;
(ii) removing any protecting groups on $R^1$; or
(iii) converting the product to a salt.

Suitable formylating agents include the reagent 4-formyl-2-methyl-1,3,4-thiadiazolin-5-thione (see H. Yazawa and S. Goto, Tetrahedon Letters, 1985, 26, 3703-3706), or mixed anhydrides such as formic acetic anhydride. The reaction may suitably be carried out in a temperature in the range —50° C. to 30° C. in aprotic solvent such as, for example, dichloromethane, chloroform, dimethylformamide, tetrahydrofuran, hexamethylphosphoramide, or dimethylsulfphoxide, in the presence of a tertiary base. A preferred tertiary base employed in the reaction is a base of the pyridine type, such as pyridine, lutidine or picoline.

Suitable readily removable carboxyl protecting groups for the group —$CO_2R^X$ in formula (V) include salt and ester derivatives of the carboxylic acid. The derivative is preferably one which may readily be cleaved. Suitable ester-forming carboxyl-protecting groups are those which may be removed under conventional conditions. Such groups for $R^X$ include benzyl, p-methoxybenzyl, benzoylmethyl, p-nitrobenzyl, 4-pyridylmethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, p-toluenesulphonylethyl, methoximethyl, a silyl, stannyl or phosphorus-containing group, an oxime radical of formula —N=$CHR^7$ where $R^7$ is aryl or heterocyclic, or an in vivo hydrolysable ester radical such as defined above.

Suitable groups for $R^X$ include diphenylmethyl; t-butyl; and tri($C_{1-6}$)alkylsilyl groups.

Preferred groups for $R^X$ are diphenylmethyl and trimethylsily.

A carboxyl group may be regenerated from any of the above esters by usual methods, appropriate to the particular $R^X$ group, for example, acid- and base-catalysed hydrolysis, or by enzymically-catalysed hydrolysis, or by hydrogenolysis.

One process for preparing compounds within formula (V) is disclosed in or is analogous to processes disclosed in European Patent Application No. 82330821.1 (Publication No. 0 071 395). A further process for preparing compounds within formula (V) comprises treating a compound of formula (IVA) with ammonia.

It will be apparent from the above that a process for preparing compounds of formula (I) comprises formamidylating a compound of formula (VA):

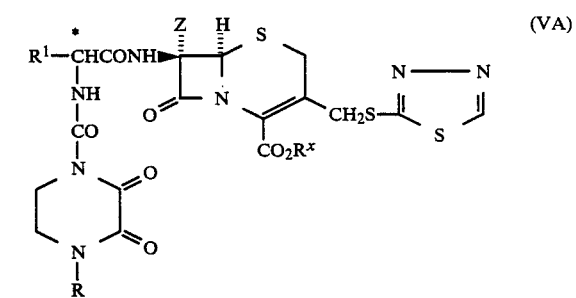

wherein Z is $SR^6$, $SOR^6$ or $NH_2$; and R, $R^1$, $R^6$, $R^X$ and * are as hereinbefore defined.

As used herein the term 'formamidylating' deontes converting the groups Z into the group —NHCHO.

The compounds of formula (I) may also suitably be prepared by reacting a compound of formula (VI):

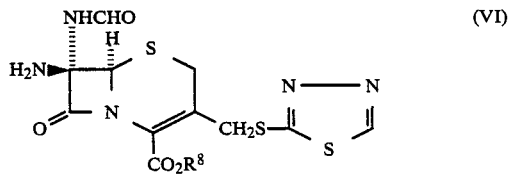

wherein $R^8$ s as hereinbefore defined; the amino group is optionally substituted with a group which permits acylation to take place; and any reactive groups may be protected; with an N-acylating derivative of an acid of formula (VII):

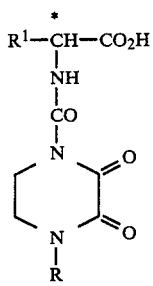

(VII)

wherein R, $R^1$ and * are defined with respect to formula (I) and wherein any reactive groups may be protected; and thereafter, if necessary, carrying out one or more of the following steps:

(i) converting a group $R^8$ into another group $R^8$;
(ii) removing any protecting groups on $R^1$;
(iii) converting the product into a salt.

The compounds of formula (IA) may be prepared by a similar process, which process further comprises, if necessary, the step of converting the product into a pjharmaceutically acceptable salt or pharmaceutically acceptable in vivo hydrolysable ester.

Preferred compounds of formula (VI) include salts and esters in which $R^8$ is $R^x$ as hereinbefore defined and in particular in which $R^8$ is diphenylmethyl, a substituted ammonium cation, especially triethylammonium, or a silyl group, especially trimethylsilyl.

Particularly preferred groups for $R^8$ are triethylammonium and trimethylsilyl. Salt and ester derivatives bearing these groups are conveniently prepared in situ from compounds of formula (VI) that are more readily isolated, for example from the acid of formula (VI) wherein $R^8$ is hydrogen (or a zwitterionic form thereof), before addition of the N-acylating derivative of the acid of formula (VII).

Suitable groups which permit acylation to take place and which are optionally present on the amino group of the starting material of the formula (VI) include N-silyl, N-stannyl and N-phosphorus groups, for example trialkylsilyl groups such as trimethylsilyl, trialkyltin groups such as tri-n-butyltin, groups of formula —P.$R^9R^{10}$ wherein $R^9$ is an alkyl, haloalkyl, aryl, aralkyl, alkoxy, haloalkyl, aryl, aralkyl, alkoxy, haloalkoxy, aryloxy, aralkyloxy or dialkylamino group, $R^{10}$ is the same as $R^9$ or is halogen or $R^9$ and $R^{10}$ together form a ring; suitable such phosphorus groups being —P(OC$_2$H$_5$)$_2$, —P(C$_2$H$_5$)$_2$,

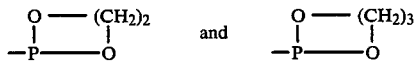

A preferred group which may be introduced onto the amino group in the compound of formula (VI) is trimethylsilyl.

An appropriate reactive N-acylating derivative of the acid (VII) is employed in the above process.

Suitable N-acylating derivatives include an acid halide, preferably the acid chloride or bromide. Acylation with an acid halide may be effected in the presence of an acid binding agent, for example a tertiary amine (such as pyridine or dimethylaniline), molecular sieves, or an inorganic base (such as calcium carbonate or dodium bicarbonate) or an oxirane, which binds hydrogen halide liberated in the acylation reaction. The oxirane is preferably a (C$_{1-6}$)-1,2-alkylene oxide-such as ethylene oxide or propylene oxide. The acylation reaction using and acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

Preferred solvents include tetrahydrofuran, and anhydrous chlorinated hydrocarbons, especially dichloromethane.

The acid halide may be prepared by reacting the acid (VII) or a salt or suitable derivative thereof with a halogenating (eg chlorinating or brominating) agent such as phosphorus pentachloride, phosphorus oxychloride, thionyl chloride, oxalyl chloride, or phosgene.

Suitable derivatives of the acid (VII) which may be employed in the above process include labile esters such as silyl esters. Suitable silyl esters include, for example, tri(C$_{1-6}$)alkyl silyl esters, especially the trimethylsilyl ester.

Alternatively, the N-acylating derivative of the acid (VII) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric, phosphorous, and phosphinic acids or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (VII) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (VII) with an oxime.

Other reactive N-acylating derivatives of the acid (VII) include the reactive intermediates formed by reaction in situ with a condensing agent such as a carbodiimide, for example, N,N'-diethyl-, di-n-propyl-or diisopropylcarbodiimide, N,N'-di-cyclohexylcarbodiimide, or N-ethyl-N'-[3-dimethylamino)propyl]-carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinole, such as N-ethoxycarbonyl 2-ethoxy-1,2-dihydroquinoline. Other condensing agents include Lewis acids (for example BBr$_3$ - C$_6$H$_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

The compounds of formula (I) may also suitably be prepared by reacting a compound of formula (VIII):

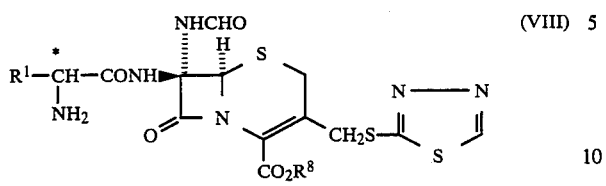

wherein $R^1$, $R^8$ and * are as hereinbefore defined and the α-amino group is optionally substituted with a group which permits acylation to take place, and any reactive groups may be protected; with an N-acylating derivative of an acid of formula (IX):

wherein R is as hereinbefore defined and wherein any reactive groups may be protected; and thereafter, if necessary, carrying out one or more of the following steps:

(i) converting the group $R^8$ into another group $R^8$;
(ii) removing any protecting groups on $R^1$;
(iii) converting the product into a salt.

The compounds of formula (VIII) herein which are inter alia intermediates for the compounds of formula (I) as hereinbefore defined may be prepared by reacting a compound of formula (VI) with an N-acylating derivative of an acid of formula (X):

wherein $R^1$ and * are as hereinbefore defined and $R^{11}$ is an amino-protecting group and thereafter removing protecting group $R^{11}$.

Suitable amino-protecting groups $R^{11}$ are those well-known in the art which may be removed under conventional conditions without disruption of the remainder of the molecule.

Examples of amino-protecting groups for $R^{11}$ include benzyl optionally substituted in the phenyl ring by one or two substituents selected from $C_{1-4}$ alkyl, $C_{1-4}$ alkoxycarbonyl optionally substituted by a phenyl or biphenylyl group, for example tert-butoxycarbonyl or 1-methyl-1-(4-biphenylyl)ethoxycarbonyl; benzyloxycarbonyl optionally substituted as for benzyl above; allyloxycarbonyl; or trityl.

Compounds of formula (VIII) may also be prepared by reacting a compound of formula (VI) with an N-acylating derivative of an acid of formula (XA):

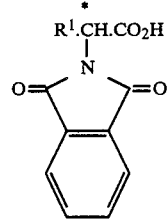

wherein $R^1$ and * are as hereinbefore defined; and thereafter converting the phthalimido group into an amino group by conventional methods.

Compounds of formula (VIII) may also be prepared by reacting a compound of formula (VI) with an N-acylating derivative of an α-azido acid of formula (XI):

wherein $R^1$ and * are as hereinbefore defined; followed by conversion of the azido group into an amino group by conventional methods, for example by ctalytic hydrogenation, or by reaction with triphenylphosphine followed by hydrolysis of the resultant phosphinimine.

In a alternative aspect, the resultant phosphinimine prepared as described above may be treated with an N-acylating derivative of an acid of formula (IX) as hereinbefore defined to provide yet a further process for preparing compounds of formula (I). In this reaction the N-acylating derivative of the acid of formula (IX) is preferably the acid chloride.

The intermediate compound of formula (VI) as hereinbefore defined may suitably be prepared by reacting a compound of formula (XII) or an acid addition salt thereof:

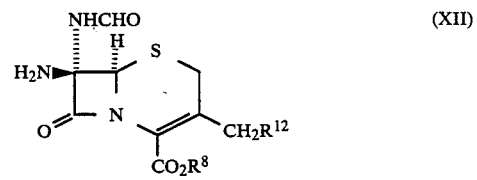

wherein $R^8$ is as hereinbefore defined and $R^{12}$ is a leaving group; with a thiol of formula (XIII):

with the proviso that when $R^{12}$ is an acyloxy group —$CO_2R^8$ must be in the free acid form or a salt thereof; and thereafter, if necessary, converting the group $R^8$ into another group $R^8$.

Suitaable leaving groups $R^{12}$ include halogen such as iodide or bromide or an acyloxy groups such as, for example the acetoxy group.

A preferred group for R is acetoxy.

A preferred acid addition salt of the compound of formula (XII) is the trifluoroacetate.

The thiol may be reacted as the free compound or a salt with an alkali metal such as sodium or potassium. This reacion is desirably conducted in a solvent. For example, use can be made of water, or organic solvents inert to the starting compounds, such as dimethylformamide, dimethylacetamide, dioxane, acetone, alcohol, dichloromethane, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carred out at a selected temperature within the range of 0° to 100° C. for a selected time of a few hours to several days. The reaction is desirably conducted between pH 3 and 7.

To prevent oxidation of the thiol it is advantageous to carry out the reaction in an inert gaseous atmosphere, e.g. argon gas.

The compounds of the present invention of formula (I) may also suitably be prepared by reacting a compound of formula (XIV):

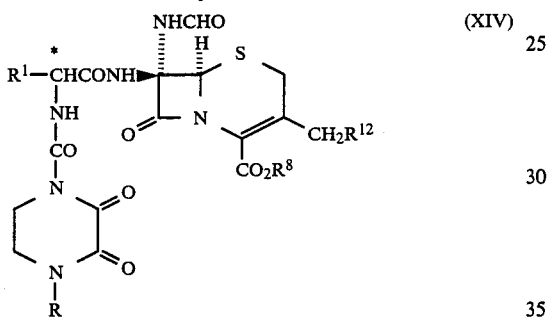

wherein R, $R^1$, $R^8$, $R^{12}$ and * are as defined hereinbefore, and wherein any reactive groups may be protected; with a thiol of formula (XIII) with the proviso that when $R^{12}$ is an acyloxy group —$CO_2R^8$ must be in the free acid form or a salt thereof.

Suitable leaving groups $R^{12}$ include halogen such as iodide or bromide or an acyloxy groups such as, for example the acetoxy group.

The thiol (XIII) may be reacted as the free compound or a salt with an alkali metal such as sodium or potassium under the same conditions as specified above for the preparation of compounds of formula (VI).

To prevent oxidation of the thiol it is advantageous to carry out the reaction in an inert gaseous atmosphere, e.g. argon gas.

From the foregoing it will be appreciated that compounds of formula (VI) and protected derivatives thereof are valuable intermediates, which are novel and form another preferred aspect of the present invention.

Specific compounds within formula (VI) that may be readily isolated include the following:
Diphenylmethyl 7β-amino-7α-formamido-3-[(1,3,4-thiadiazol-2-yl)thiometyl]ceph-3-em-4-carboxylate.
7β-Amino-7α-formamido-3-[(1,3,4-thiadiazol-2-yl)thiomethyl]ceph-3-em-4-carboxylic acid.
Sodium 7β-amino-7α-formamido-3-[(1,3,4-thiadiazol-2-yl)-thiomethyl]ceph-3em-4-carboxylate.

Compounds of formula (VI) that may be more conveniently prepared in situ include:
Triethylammonium 7β-amino-7α-formamido-3-[(1,3,4-thiadiazol-2-yl)thiomethyl]ceph-3-em-4-carboxylate.
Trimethylsilyl 7β-amino-7α-formamido-3-[(1,3,4-thiadiazol-2-yl)thiomethyl]ceph-3-em-4-carboxylate.

It will be appreciated that 7β-amino-7α-formamido-3-[(1,3,4-thiadiazol-2-yl)thiometyl]ceph-3-em-4-carboxylic acid, i.e. the compound of formula (VIA) below, may also be represented as NVIB) below and indeed will normally exist in such a zwitterionic form. An alternative chemical name for the compound is thus 7β-ammonio-7α-formamido-3-[(1,3,4-thiadiazol-2-yl)thiomethyl]ceph-3-em-4-carboxylate.

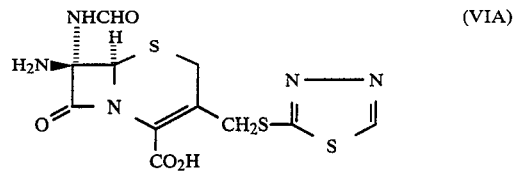

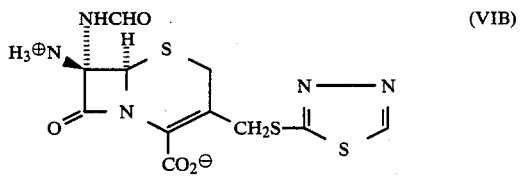

Compound (VIB) is a valuable intermediate that may be conveniently prepared from the trifluoroacetic acid salt of a compound of formula (XII) as hereinbefore defined, wherein $R^8$ is hydrogen and $R^{12}$ is acetoxy, by treatment with 2-mercapto-1,3,4-thiadiazole in aqueous solution at a pH of approximately 3.5; and (i) subsequent acidification to a pH of approximately 1.5; or (ii) isolating the product via the corresponding sodium salt (VI; $R^8$=Na) or other alkaly metal or alkaline earth metal salt, followed by acidification to a pH of approximately 1.5.

Compound (VIB) [or (VIA)] may be converted into salt and ester derivatives of the formula (VI) by conventional salifaication and esterification procedures. Conveniently, in the process for the preparation of compounds of formula (I) from compounds of formula (VI) as hereinbefore described, such salts and esters are prepared in situ. Preferred salts and esters for use in this process may be prepared by treatment of (VIB) with amines, especially triethylamine, or silylating agents such as N-methyl-N-trimethylsilyltrifluoroacetamide, N,O-bis(trimethylsilyltrifluoroacetamide), N,N'-bis (trimethylsilyl)urea, N,N-bis (trimethylsilyl) -formamide, hexamethyldisilazane, and N,O-bistrimethylsilylacetamide, especially the latter.

The above process may advantageously but optionally be carried out in the presence of a small quatity, for example 0.1 equivalnets, of a silyl halide, for example a tri($C_{1-6}$)alkylsilyl halide, especially trimethylsilyl chloride.

Silylation may also be conveniently effected by treatment of (VIB) with one or more equivalents of a silyl halide, preferably trimethylsilyl chloride, in the presence of an acid scavenger such as an organic base, for example pyridine.

The antibiotic compounds of the present invention are active against a wide range of gram-negative and Gram-positive organisms including E. coli such as. for example ESS, JT4, JT425 and NTC 10418; Pseudomonas Spp. such as *Ps. aeruginosa* for example 10662 and Dalgleish; *Serratia marcescens* US32; *Klebsiella aerogenes* A; *Enterobacter cloacae* N1; *P. mirabilis* such as, for example C977 and 889; *P. morganii; P. rettgeri; B. subtilis; Staph aureus* such as, for example Oxford and Russell; *N. catarrhalis* 1502; *Strep faecalis* I; *β-Haemolytic Strep* CN10.

The following Examples illustrate the preparation and biological activity of the compounds of the present invention.

The compound named in the following examples as 7-beta-amino-7alpha-formamidocephalosporanic acid trifluoroacetic acid salt was prepared as described in Example 34(E) of European Patent Application &ublication No. 0 071 395.

Example 1

Sodium 7β-[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate.

(a) Diphenylmethyl 7β-Amino-7α-formamido-3-[(1,3,4-thiadiazol-2-yl)thiomethyl]ceph-3-em-4-carboxylate 7β-Amino-7α-formamidocephalosporanic acid, trifluoroacetic acid salt (277 mg, 0.647 mmol) in water (8 ml) and acetone (4 ml) was treated with saturated sodium hydrogen carbonate to pH 6.5. 2-Mercapto-1,3,4-thiadiazole (101 mg, 0.647 mmol) was added and the pH adjusted to 3.5 with 5N—HCl. The solution was heated at 60° C. under argon for 6h, cooled and pH adjusted to 2.0 using 5N—HCl. The solvent was evaporated off, the residue dried in vacuo for 1h., and then triturated in acetonitrile (20 ml). The resulting suspension was treated with excess diphenyldiazomethane. After 24h, the mixture was treated with acetic acid until the purple colour discharged. The mixture was poured into ethyl acetate-water and the separated organic layer washed successively with sodium hydrogen carbonate solution, brinde, dried (MgSO4) and evaporated. The residue was chromatographed on silica gel to give the title compound (254 mg, 70%); $v_{max}$ (CHCl$_3$) 3320, 1780, 1720, and 1690cm$^{-1}$; δ(CDCl$_3$; major rotamer only) 2.45br (2H,NH$_2$) 3.57 and 3.77 (together 2H, ABq, J 16.9Hz, 2-CH$_2$), 4.34 and 4.62 (together 2H, ABq, J 13.4Hz, 3'-CH$_2$), 5.17 (1H,s,6-H), 6.38br (1H,s,NH.CHO), 6.99 (1H,s,CH.Ph$_2$), 7.2–7.6 (together 10H,m, aromatics), 8.26 (1H,s,NH.CHO) and 8.96 (1H,s,thiadiazole -H); F.A.B. (thioglycerol) MH+540.

(b) Diphenylmethyl 7β-[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate Freshly prepared D-2-(3,4-diacetoxyphenyl)-2-[(4-ethyl-2,3-dioxopiperazin-1-yl)carbonylamino]acetyl chloride, generated by the treatment of the corresponding acid (148 mg 0.340 mmol) with oxalyl chloride (86 mg, 0.679 mmol) in dry dichloromethane (3 ml) containing N,N-dimethylformamide (1/5 drop) for 2h, was taken up in dry dichloromethane (2 ml) and added to a stirred solution of diphenylmethyl 7β-amino-7α-formamido-3-[(1,3,4-thiadiazol-2-yl)thiomethyl]ceph-3-em-4-carboxylate (122 mg, 0.226 mmol), followed by pyridine (18.2 mg, 0.226 mmol) at 0° C. After 52 minutes the mixture was washed successively with dilute aqueous sodium hydrogen carbonate, dilute hydrochloric acid and saturated brine, dried (MgSO$_4$) and evaporated. The residue was chromatographed on silica gel to give the title compound (151 mg, 70%) as a white solid; $v_{max}$ (CHCl$_3$) 3400, 1780, 1720, 1690 and 1505cm$^{-1}$; δ[(CD$_3$)$_2$CO]1.17 (3H,t,J 7Hz,N. CH$_2$.CH$_3$), 2.24 and 2.26 (each 3H,s, 2xOCOCH$_3$), 3.02 and 3.30 (together 2H, ABq,J 16Hz,2-CH$_2$),3.51 (2H,q, J 7Hz, N.CH$_2$.CH$_3$), 3.6–3.8(together 2H, m, N.CH$_2$.CH$_2$.N), 4.0–4.1 (together 2H, m, N.CH$_2$.N), 4.29 and 4.77 (together 2H,ABq, J 13Hz, 3'-CH$_2$), 5.30 and 5.34 (together 1H, each s, 6-H, major and minor rotamer respectively), 5.76(1H, d, J 7Hz,NH.CH.CO), 6.93 (1H,s,CH.Ph$_2$), 7.15–7.7 (together 13H,m, aromatics), 8.30 (1H,d, J 1Hz, NH.CHO, major rotamer), 8.55br, 8.87br, 9.16br (together 2H, 2xNH), 9.26 and 9.34 (together 1H, each s, thiadiazole-H, major and minor rotamer respectively), and 10.12(1H,d,J 7Hz, CH.NH.CO); [F.A.B (thioglycerol) MH+957].

(c) Sodium 7β-[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate A solution of diphenylmethyl 7β-[D-2-(3,4-diacetoxyphenyl)-2-[(4-ethyl-2,3-dioxopiperazin-1-yl)carbonylamino]acetamido]-7α-formamido-3-[(1,3,4-thiadiazol-2-yl)thiometyl]ceph-3-em-4-carboxylate (149 mg, 0.146 mmol) and anisole (474 mg, 4.39 mmol) in dichloromethane (3 ml) at ice bath temperature was treated with trifluoroacetic acid (501 mg, 4.39 mmol). After 30 min., the solution was evaporated to dryness and the residue triturated with dry ether to give a white solid which was suspended in water and the pH adjusted to 6.6 with dilute sodium hydrogen carbonate. Chromatography on Diaion HP20SS and lyophilisation of the product-containing fractions (HPLC monitoring) gave the title compound (98 mg, 77%) as an amorphous white solid; $\lambda_{max}$(H$_2$O) 263(ε 13,700); $v_{max}$ (KBr) 3400, 3000, 1770, 1710, 1680, 1635, 1610, and 1500 cm$^{-1}$; δ(D$_2$O) (major rotamer only) 1.17 (3H,t,J 7.2Hz, N.CH$_2$. CH$_3$), 2.30(6H,s,2xOCOCH$_3$), 2.95 and 3.36 (together 2H, ABq, J 16.7Hz, 2-CH$_2$),3.49(2H,q,J 7.2Hz, N.CH$_2$.CH$_3$),3.6–3.8(2H,m, N.CH$_2$.CH$_2$.N),3.9–4.1 (together 3H, m, N.CH$_2$.CH$_2$.N and high-field arm of 3'-CH$_2$ ABq), 4.36(1H,d,J 13.8Hz, low-field arm of 3'-CH$_2$ABq), 5.24 (1H,s,6-H), 5.52(1H,s, CO.CH.NH), 7.2–7.6 (together 3H, m, aromatics), 8.12 (1H,s,NH.CHO), and 9.35(1H,s,thiadiazole-H); [F.A.B. (thioglycerol) MH+813].

Example 2

Sodium 7β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate To a stirred solution of sodium 7β-[D-2-(3,4-diacetoxyphenol)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate (40 mg, 0.049 mmol) in water (5 ml) at pH 8.0 was added sodium sulphite (15.5 mg, 0.123 mmol) at room temperature. The pH was maintained at 8.5 (using 2.5% w/v solution of sodium carbonate) and the progress of reaction was monitored by HPLC. When all starting material was depleted, the pH of the reaction mixture was adjusted to 6.7, and the mixture purified by chromatography on Diaion HP20SS. The product containing fractions (HPLC monitoring) were combined, concentrated and the concentrate lyophilised to afford the title compound (27 mg, 75%) as an amorphous white solid; $\lambda_{max}$ (H$_2$O)268 nm ($\epsilon$ 12,400); $\nu_{max}$ 3400, 1767, 1710, 1675, 1601, 1505, and 1396 cm$^{-1}$; $\delta$(D$_2$O) 1.17 (3H, t, J 7Hz, N.CH$_2$.CH$_3$), 3.05 and 3.37 (together 2H, ABq, J 17Hz, 2-CH$_2$), 3.50 (2H, q, J 7Hz, N.CH$_2$.CH$_3$), 3.53–3.75 (2H, m, N.CH$_2$.CH$_2$.N), 3.9–4.1 (together 3H, m, N.CH$_2$CH$_2$.N and high field arm of 3'-CH$_2$ ABq), 4.35 and 4.47 (together 1H, each d, J 14Hz, low-field arm of 3'-CH$_2$ ABq, major and minor rotamer respectively), 5.24 (1H,s, 6-H), 5.31 (1H, s, CO.CH.NH). 6.80–6.95 (together 3H,m,aromatics), 8.10 and 8.41 (together 1H, each s, NH.CHO, major and minro rotamer respectively), and 9.35 (1H,s, thiadiazole-H); [F.A.B. (thioglycerol) MH$^+$ 729].

Example 3

Sodium 7β-[D-2-[(4-Ethyl-2,3-dioxopiperazin-1-yl)carbonylamino]-2-phenylacetamido]-7α-formamido-3-[(1,3,4-thiadiazol-2-yl)thiomethyl]ceph-3-em-4-carboxylate (a) Diphenylmethyl 7β-[D-2-[(4-Ethyl-2,3-dioxopiperazin-1-yl)carbonylamino]-2-phenylacetamido]-7α-formamido-3-[(1,3,4-thiadiazol-2-yl)thiomethyl]ceph-3-em-4-carboxylate Freshly prepared D-2-[(4-ethyl-2,3-dioxopiperazin-1-yl)carbonylamino]-2-phenylacetyl chloride, generated by the treatment of the corresponding acid (26 mg, 0.082 mmol) with oxalyl chloride (20.7 mg, 0.163 mmol) in dry dichloromethane (2 ml) containing N,N-dimethylformamide (1/5 drop) for 2 h, was taken up in dry dichloromethane (1 ml) and added to a stirred solution of diphenylmethyl 7β-amino-7α-formamido-3-[(1,3,4-thiadiazol-2-yl)thiomethyl]ceph-3-em-4-carboxylate (22 mg, 0.0404 mmol), followed by pyridine (3.2 mg, 0.0408 mmol). After 90 min, the mixture was diluted with dichloromethane and washed successively with dilute aqueous sodium hydrogen carbonate, dilute hydrochloric acid, and saturated brine, dried (MgSO$_4$) and evaporated. The residue was chromatographed on silica gel to give the tittle compound (26 mg, 64%) as a yellow syrup; $\nu_{max}$ (CHCl$_3$) 3280, 3000, 1785, 1720 and 1690 cm$^{-1}$; $\delta$[(CD$_3$)$_2$CO[ inter alia (major rotamer only) 1.19 (3H, t, J 7 Hz, N.CH$_2$CH$_3$), 3.18 and 3.31 (together 2H, ABq, J 15.4 Hz, 2-CH$_2$), 3.52 (2H, q,J 7 Hz, N.CH$_2$.CH$_3$), 3.6–3.8 and 3.95–4.1 (each 2H, m, N.CH$_2$.CH$_2$.N), 4.40 and 4.70 (together 2H, ABq, J 12.8 Hz, 3'-CH$_2$), 5.29 (1H, s, 6-H), 5.73 (1H, d, J 7 Hz, NH.CH.CO), 6.94 (1H, s, CH.Ph$_2$), 7.1–7.7 (15H, m, aromatics), 8,30 (1H, d, J ca. 0.5 H,z NH.CHO), 8.55 br and 8.73 br (each 1H, s, 2 x CO.NH.C), 9.32 (1H, s, thiadiazole H), and 10.05 (1H, d, J 7 Hz, CH.NH.CO).

(b) Sodium 7β-[D-2-[(4-Ethyl-2,3-dioxopiperazin-1yl)carbonylamino]-2-phenylacetamido]-7α-formamido-3-[(1,3,4-thiadiazol-2-yl)thiomethyl]ceph-3-em-4-carboxylate A solution of diphenylmethyl 7β-[D-2-[(4-ethyl-2,3-dioxopiperazin-1-yl)carbonylamino]-2-phenylacetamido]-7α-formamido-3-[(1,3,4-thiadiazol-2-yl)thiomethyl]ceph-3-em-4-carboxylate (24 mg, 0.0286 mmol) and anisole (32.3 mg, 0.299 mmol) in dichloromethane (1.5 ml) at ice bath temperature was treated with trifluoroacetic acid (34.2 mg, 0.299 mmol). After 30 min, the solution was evaporated to dryness and the residue triturated with dry ether to give a white solid which was suspended in water and the pH adjusted to 6.7 with dilute sodium hydrogen carbonate solution. The resulting solution was chromatographed on Diaion HP20SS and the product-containing fractions (HPLC monitoring) combined, concentrated and lyophilised to afford the title compound as an amorphous white solid (7 mg, 35%); $\nu_{max}$. (KBr) 3424, 2973, 1769, 1676, 1635, 1607, 1521 and 1395 cm$^{-1}$; $\delta$(D$_2$O) (major rotamer only) 1.18 (3H, t, J 7.2 Hz, N.CH$_2$.CH$_3$), 3.00 and 3.42 (together 2H, ABq, J 17 Hz, 2-CH$_2$), 3.50 (2H, q, J 7.2 Hz, N.CH$_2$.CH$_3$), 3.60–3.80 (2H, m, N.CH$_2$.CH$_2$.N), 3.90–4.15 (together 3H, m, N.CH$_2$.CH$_2$N and high-field arm of 3'-CH$_2$), 4.41 (1H, d, J 14 Hz, low-field arm of 3'-CH$_2$ ABq), 5.22 (1H, s, 6-H), 5.50 (1H, s, NH.CH.C), 7.4–7.6 (5H, m, Ph), 8.11 (1H,s, NH.CHO), and 9.38 (1H,s, thiadiazole H); [FAB (thioglycerol) MH$^+$ 697].

Example 4

Sodium 7α-[D-2-(4-Acetoxyphenyl)-2-[(4-ethyl-2,3-dioxopiperazin-1-yl)carbonylamino]acetamido]-7α-formamido-3-[(1,3,4-thiadiazol-2-yl)thiomethyl]-ceph-3-em-4-carboxylate (a) Diphenylmethyl 7β-[D-2-(4-Acetoxyphenyl)-2-[(4-ethyl-2,3-dioxopiperazin-1-yl)carbonylamino]-acetamido]-7α-formamido-3-[(1,3,4-thiadiazol-2-yl)thiomethyl]ceph-3-em-4-carboxylate D-2-(4-Acetoxyphenyl)-2-[(4-ethyl-2,3-dioxopiperazin-1-yl)carbonylamino]acetyl chloride, freshly prepared by treatment of the corresponding acid (612 mg; 1.62 mmol) with oxalyl chloride (445 mg, 3.24 mmol) in dry dichloromethane (10 ml) containing a catalytic quantity of dry N,N-dimethylformamide, was dissolved in dry dichloromethane (10 ml). A portion of the resulting solution (7.14 ml, equivalent to 1.16 mmol) was added, dropwise over 10 min, to a stirred solution of diphenylmethyl 7β-amino-7α-formamido-3-[(1,3,4-thiadiazol-2-yl)thiomethyl]ceph-3-em-4-carboxylate (500 mg, 0.93 mmol) in dry dichloromethane (10 ml) at 0° C., followed by the addition of pyridine (92 mg, 1.16 mmol) in dry dichloromethane (5 ml). The reaction was monitored by t.l.c. After 50 min at 0° C., a further portion of the acid chloride preparation (1.43 ml, 0.23 mmol) and pyridine (18 mg, 0.23 mmol) were added, and the mixture was allowed to warm to room temperature. After 0.5 h the mixture was diluted with dichloromethane (30 ml), then washed successively with saturated sodium bicarbonate solution, dilute hydrochloric acid, water and brine. The organic phase was dried (anhydrous MgSO$_4$), filtered and evaporated. Silica gel chromatography of the crude mixture grave the title compound (550 mg; 66%) as a white solid; $\nu_{max}$ (KBr) 3360 (sh), 3282, 1776, 1758, 1720 (sh) and 1689 cm$^{-1}$; $\delta_H$ [10:1,(CD$_3$)$_2$SO/D$_2$O](major rotamer) 1.06 (3H, t,J 7.1 Hz), 2.22 (3H, s), 3.09 (1H, higher field arm of ABq, J 16.3 Hz), 3.30–3946 (3H, m), 3.47–3.60 (2H, m), 3.80–3.95 (2H, m), 4.18 and 4.52 (together 2H, ABq, J 13.9 Hz), 5.20 (1H,s), 5.66 (1H, s), 6.82 (1H, s), 7.0–7.6

(14H, m), 8.11 (1H, s), and 9.41 (1H, s); [FAB (+ve ion) MH+ 899].

(b) Sodium 7β-[D-2-(4-Acetoxyphenyl)-2-[(4-ethyl-2,3-dioxopiperazin-1-yl)carbonylamino]acetamido]7α-formamido-3-[(1,3,4-thiadiazol-2-yl)thiomethyl]-ceph-3-em-4-carboxylate Diphenylmethyl 7β-[D-2-(4-acetoxyphenyl)-2-[(4-ethyl-2,3-dioxopiperazin-1-yl)carbonylamino]acetamido-7α-formamido-3-[(1,3,4-thiadiazol-2-yl)thiomethyl]ceph-3-em-4-carboxylate (530 mg, 0.59 mmol) in dry dichloromethane (50 ml) at 0° C. was treated with anisole (3.823 g, 35.4 mmol) and trifluoroacetic acid (2.018 g, 17.7 mmol). The reaction was monitored by t.l.c. After ca. 1.25 h the mixture was evaporated at reduced pressure and the residue treated with dry toluene (ca. 5 ml) and re-evaporated. After briefly drying in vacuo, the residue was triturated with anhydrous ether (x 3). The resulting solid was dried in vacuo, then suspended in water (7 ml), and saturated sodium bicarbonate solution was added to pH 7.0. The crude mixture was chromatographed on Diaion HP20SS resin, eluting initially with water then acetone/water mixtures. The product containing eluant was concentrated at reduced pressure and lyophilisation of the concentrate grave the tittle compound (206 mg; 46%); $\lambda_{max}$ (H$_2$O) 262 nm ($\epsilon_m$ 14977); $\gamma_{max}$ (KBr) 3410 (sh), 3295, 1764, 1710 (sh), 1676 and 1606 cm$^{-1}$; $\delta_H$ (D$_2$O) (major rotamer) 1.17 (3H, t, J 7.0 Hz), 2.29 (3H, s), 2.97 and 3.37 (together 2H, ABq, J 16.8 Hz), 3.44–3.58 (2H, m), 3.59–3.80 (2H, m) 3.82–4.15 (3H, m), 4.37 (1H, lower field arm of ABq, J 13.9 Hz), 5.22 (1H, s), 5.51 (1H, s), 7.14 (2H, d, J 8.3 Hz), 7.56 (2H, d, J 8.3 Hz), 8.12 (1H, s) and 9.37 (1H, s). (FAB (thioglycerol) MH+ 755).

Example 5
Sodium 7β-[D-2-[(4-Ethyl-2,3-dioxopiperazin-1-yl)-carbonylamino]-2-(4-hydroxyphenyl)acetamido]-7α-formamido-3-[(1,3,4-thiadiazol-2-yl)thiomethyl]ceph-3-em-4-carboxylate A solution of sodium 7β-[D-2-(4acetoxyphenyl)-2-[(4-ethyl-2,3-dioxopiperazin-1-yl)carbonylamino]acetamino]-7α-formamido-3-[(1,3,4-thiadiazol-2yl)thiomethyl]-ceph-3-em-4-carboxylate (100 mg, 0.133 mmol) in water (ca. 5 ml) at room temperature was treted with 2.5% (w/v) aqueous sodium carbonate solution to pH 8.0, then treated with sodium sulphite (21 mg, 0.166 mmol) in one portion. The pH of the mixture was maintained at 8.5/9.0 by further additions of 2.5% (w/v) aqueous sodium carbonate solution and the reaction monitored by reverse phase HPLC. After ca. 1.75 h the crude mixture was chromatographed on Diaion HP20SS resin, eluting initially with water, then acetone/water mixtures. The product containing eluant was concentrated grave the title compound (57 mg, 60%); $\lambda_{max}$ (H$_2$O) 265 nm. ($\epsilon_m$ 13757); $\lambda_{max}$ (KBr) 3395 (sh), 3290, 1769, 1710 (sh), 1675 and 1610 cm$^{-1}$; $\delta_H$ (D$_2$O) (major rotamer) 1.16 (3H, t, J 7.2 Hz), 3.02 and 3.41 (together 2H, ABq, J 16.8 Hz), 3.48 (2H, q, J 7.2 Hz) 3.55–3.75 (2H, m), 3.80–4.10 (3H, m), 4.35 (1H, lower field arm of ABq, J 13.9 Hz), 5.22 (1H, s), 5.39 (1H, s), 6.88 (1H, d, J 8.6 Hz), 7.37 (1H, d, J 8.6 Hz), 8.09 (1H, s), and 9.35 (1H, s). (FAB (thioglycerol) MH+ 713, MNa+ 735).

Example 6
Sodium 7β-[D,L-2-(3-Acetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate

(a) Diphenylmethyl 7β-[D,L-2-(3-Acetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate Freshly prepared D,L-2-(3-acetoxyphenyl)-2-[(4-ethyl-2,3-dioxopiperazin-1-yl)carbonylamino]acetyl chloride, generated by treatment of the corresponding acid (420 mg, 1.11 mmol) with oxalyl chloride (283 mg, 2.22 mmol) in dry dichloromethane (5 ml) containing a catalytic quantity of N,N-dimethylformamide,was taken up in dry dichloromethane (5 ml) and added dropwise to a stirred solution of diphenylmethyl 7β-amino-7α-formamido-3-[(1,3,4-thiadiazol-2-yl)thiomethyl]-ceph-3-em-4-carboxylate (600 mg, 1.11 mmol) in dry dichloromethane (10 ml) containing pyridine (93 mg, 1.17 mmol) at 0° C. The reaction was monitored by t.l.c. After 1.5° h at 0° C. the reaction was allowed to warm to room temperature. After a further 0.5 h, the mixture was diluted with dichloromethane and washed successively with dilute hydrochloric acid, water, saturated aqueous sodium bicarbonate, water and brine. The organic phase was dried (anhydrous MgSO$_4$), filtered and evaporated. The residue was chromatogaphed on silica gel to give the title compound (503 mg, 50%). $\nu_{max}$ (CH$_2$Cl$_2$) 3275, 1790, 1770 (sh), 1720 (sh) and 1690 cm$^{-1}$; $\delta_H$ [(CD$_3$)$_2$CO] (D/L ratio ca. 3:2 ) (major rotamers) 1.17 (3H, t, J 7.5 Hz), 2.24 (1.8H, s), 2.26 (1.2H, s), 3.11 and 3.28 (together 2H, ABq, J 16.0 Hz), 3.45–3961 (2H, m), 3.62–3.80 (2H, m), 4.00–4.20 (2H, m), 4.37 (1H, higher field arm of ABq, J 13.5 Hz), 4.72 (0.6H, lower field arm of ABq, J 13.5 Hz), 4.73 (0.4H, lower field arm of ABq, J 13.5 Hz), 5.30 (1H, s), 5972 (0.6H, d, J 7.0 Hz, collapses to s on D$_2$O exch.), 5.81 (0.4H, d, J 7.2 Hz, collapses to s on D$_2$O exch.), 6.92 (1H, s), 7.00–7.80 (14H, m), 8.23 (0.4 H, d, J 1.1 Hz, collapses to s on D$_2$O exch.) 8.30 (0.6H, d, J 1.1 Hz, collapses to s on D$_2$O exch.), 8.54 (0.6H, s, exch. D$_2$O), 8.56 (0.4H, s, exch. D$_2$O), 8.67 (0.4H, s, exch. D$_2$O), 8.81 (0.6H, s, exch. D$_2$O), 9.30 (1H, s). 10.00–10.15 (1H, m, exch. D$_2$O); [FAB (+ve ion) (thioglycerol) MH+ 899].

(b) Sodium 7β-[D,L-2-(3-Acetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate A solution of diphenylmethyl 7β-[D,L-2-(3-acetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate (463 mg, 0.52 mmol) in dry dichloromethane (10 ml), at 0° C., was treated with anisole (562 mg, 5.20 mmol) followed by trifluoroacetic acid (593 mg, 5.20 mmol). The reaction was monitored by t.l.c. After 0.75 h, more anisole (562 mg, 5.20 mmol) and trifluoroacetic acid (593 mg, 5.20 mmol) were added to the mixture. After a further 0.25 h the mixture was evaporated at reduced pressure. The residue was treated with dry toluene (ca. 2 ml) and then evaporated at reduced pressure. The residue was dried in vacuo for ca. 1 h, then triturated with anhydrous ether (× 3) and the resultant solid dried in vacuo. The solid was suspended in water (ca. 5 ml) and treated with saturated aqueous sodium bicarbonate solution to pH 6.5/7.0. Chromatography of the crude mixture on Diaion HP20SS resin, eluting initially with water then acetone/water mixtures followed by lyophilisation gave the title compound (164 mg, 44%); $\lambda_{max}$ (H$_2$O) 263 nm ($\epsilon_m$ 14333); $\nu_{max}$ (KBr) 3390 (sh), 3291,1765, 1715 (sh), 1678 and 1608 cm$_{-1}$; $\delta_H$ [D$_2$O] (D/L ratio ca. 3:2) (major rotamers) 1.16 (3H, t, J 7.2 Hz), 2.29 (3H, s), 2.97 and 3.37 (together 1.2H, ABq, J 17.0 Hz), 3.04 (0.4H, higher field arm of ABq, J 13.2 Hz), 3.48 (2H, q, J 7.2 Hz; obscuring 0.4H, lower field arm of ABq), 3.58–3.80 (2H, m), 3.80–4.15 (3H, m), 4.36 (0.6H, lower field arm of ABq, J 13.9 Hz), 4.44, (0.4H, lower field arm of ABq, J 14.1 Hz), 5.13 (0.4 H, s), 5.22 (0.6H, s), 5.51 (0.6H, s), 5.55 (0.4 H, s), 7.05–7.55 (4H, m), 8.07 (0.4H, s), 8.10 (0.6H, s), 9.36 (0.6H, s) and 9.38 (0.4H, s); [FAB (+ve ion) (thioglycerol) MH+ 755].

Example 7

Sodium 7β-[D,L-2-[(4-Ethyl-2,3-dioxopiperazin-1-yl)carbonylamino]-2-(3-hydroxyphenyl)acetamido]-7α-formamido-3-[(1,3,4-thiadiazol-2-yl)thiomethyl]ceph-3-em-4-carboxylate A solution of sodium 7β-[D,L-2-(3-acetoxyphenyl)-2-[(4-ethyl-2,3-dioxopiperazin-1-yl)carbonylamino]-acetamido]-7α-formamido-3-[(1,3,4-thiadiazol-2-yl)thiometyl]-3-em-4-carboxylate (146 mg, 0.194 mmol) in 0.05 M aqueous sodium dihydrogen phosphate (10 ml) at room temperature was treated with citrus acetylesterase preparation (ex. Sigma Chemicals) (1.5 ml, equivalent to 6 mg of protein). The pH was adjusted to ca. 7.0 with ca. 0.1/0.05 M aqueous sodium hydroxide and maintained throughout the reaction. The reaction was monitored by reverse phase h.p.l.c. and after ca. 45 min deacetylation was complete. The mixture was concentrated at reduced pressure and the concentrate chromatographed on "Diaion HP20SS" resin eluting initially with water then water/acetone mixtures to give the title compound as a white amorphous solid after concentration and lyophilization of the product containing eluant (110 mg, 80%); $\lambda_{max}$ (H$_2$O) 267nm ($\epsilon_m$ 15874); $\nu_{max}$ (KBr) 3400 (sh), 3277, 1772, 1710 (sh), 1674, and 1601cm$^{-1}$; $\delta_H$ [D$_2$O](D/L ca. 2:1, major rotamers only) 1.18 (3H, t, J 7.2Hz), 2.93 (0.33H, higher field arm of ABq, J 16.5Hz), 2.98 and 3.35 (together 1.33H, ABq, J 16.6Hz), 3.50 (2H, q, J 7.2Hz; obscuring 0.33H, lower field arm of ABq), 3.60–3.80 (2H, m), 3.90–4.20 (3H, m), 4.30–4.50 (1H, m), 5.16 (0.33H, s), 5.25 (0.67H, s), 5.43 (0.67H, s), 5.48 (0.33H, s), 6.80–7910 (3H, m), 7.20–7.35 (1H, m), 8.09 (0.33H, s), 8.12 (0.67H, s), 9.38 (0.6H, s), and 9.39 (0.67H, s); [FAB (+ve ion) (thioglycerol) MH+ 713].

Example 8

Sodium 7β-Amino-7α-formamido-3-[(1,3,4-thiadiazol-2-yl)thiomethyl]ceph-3-em-4-carboxylate 7β-Amino-7α-formamidocephalosporanic acid, trifluoroacetic acid salt (271 mg, 0.631 mmol) was suspended in water (8 ml) and acetone (4 ml) and the pH adjusted to 6.5 with saturated sodium hydrogen carbonate. 2-Mercapto-1.3.4-thiadiazole (98 mg, 0.631 mmol) was added, the pH adjusted to 3.5 with 5N HCl and the solution heated under argon at 60° C. for 6h. The solution was cooled, the pH adjusted to 6.5, and the solvent evaporated off. The residue was taken up in water and chromatographed on HP20SS to give, after lyophilisation of the product-containing fractions, the title product (129 mg; 52%); $\nu_{max}$. (KBr) 3359, 1756, 1669, and 1603cm$^{-1}$; $\delta_H$ (D$_2$O) (major rotamer only) 3.43 and 3.76 (2H, ABq, J 17.5Hz), 4.03 and 4.47 (2H, ABq, J 13.8Hz), 5.14 (1H, s), 8.16 (1H, s), and 9.41 (1H, s). [F.A.B. +ve ion (Thioglycerol) MH$^{30}$ 396, MNa+ 418].

Example 9

7β-Ammonio-7α-formamido-3-[(1,3,4-thiadiazol-2-yl)thiomethyl]ceph-3-em-4-carboxylate

Method A

Sodium 7β-amino-7α-formamido-3-[(1,3,4-thiadiazol-2-yl)thiomethyl]ceph-3-em-4-carboxylate (500 mg, 1.27 mmol) in water (3 ml) was acidified to pH 1.5 with 5N HCl. The mixture was cooled in ice/water bath for ca. 15 min. The precipitate was filtered off, washed with acetone, then dried in vacuo (423 mg, 90%) (Found: C, 35.1; H, 2.8; N, 18.1; S, 25.8; C$_{11}$H$_{11}$N$_5$O$_4$S$_3$ requires C, 35.4; H, 3.0; N, 18.7; S, 25.8%); $\lambda_{max}$. (H$_2$O) 269nm ($\epsilon_m$ 13731); $\nu_{max}$. (KBr) 3182, 2505, 2062, 1799, 1770 (sh), 1692, 1680 (sh), and 1575 cm$^{-1}$; $\delta_H$(d$_6$-DMSO) (major rotamer) 3.50 and 3.71 (2H, ABq, J 13.2Hz), 4.23 and 4.54 (2H, ABq, J 13.2Hz), 5.03 (1H, s), 8.03 (1H, d, J 1.4Hz, collapses to s on exch.), 9.10 (1H, broad s, exch. D$_2$O), and 9.56 (1H, s). [F.A.B. +ive ion (3-nitrobenzyl alcohol/sodium ions) MNa$^{30}$ 396, MNa$^+$$_2$ 418].

Method B

7β-Amino-7α-formamidocephalosporanic acid, trifluoroacetic acid salt (21.5 g; 0.05 mol) was suspended in water (500 ml) and the pH adjusted to 6.5 with 1M-sodium hydrogen carbonate solution. 2-Mercapto-1,3,4-thiadiazole (6.3 g; 0.053 mol) was added, the pH adjusted to 4 with 2M-hydrochloric acid, and the reaction mixture heated to 60° C. under inert atmosphere. After readjusting the pH to 4, the solution was heated at 60° C. for 4.25 h, then cooled and concentrated to reduced volume. The aqueous solution was acidified to pH 1.5 with 2M-hydrochloric acid and the precipiate filtered off. The yellow-orange solid was washed with small portions of water, then acetone, and dried in vacuo to yield the title compound (13.2 g; 71%).

Example 10

Sodium 7β-[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate

Method A

Triethylamine (19.8 mg, 0.196 mmol) was added in one portion to a stirred suspension of 7β-ammonio-7α-formamido-3-[(1,3,4-thiadiazol-2-yl)thiomethyl]ceph-3-em-4-carboxylate (73 mg, 0.196 mmol) in methanol (4 ml) at ambient temperature. The resultant solution was filtered and the filtrate evaporated in vacuo to afford a foam. A stirred suspension of this foam in dry dichloromethane (2.5 ml) was treated with a solution of D-2-(3,4-diacetoxyphenyl)-2-[(4-ethyl-2,3-dioxopiperazin-1-yl)carbonylamino]acetyl chloride (prepared as described in Example 1(b); 0.49 mmol) in dry dichloromethane (2.5 ml). After 30 min. water (5 ml) was added to the reaction vessel, the mixture stirred vigorously, and the pH adjusted to 6.8 using saturated aqueous sodium hydrogen carbonate. The separated organic phase was re-extracted with water (5 ml). The combined aqueous extracts were passed down an Amberlite IR120 (Na) column, eluting with water. The product-containing fractions (HPLC monitoring) were combined and purified on Diaion HP20SS resin eluting initially with water, then acetone/water mixtures. The product-containing eluant was concentrated at reduced pressure and the concentrate lyophilised to give the product (70 mg; 46%) as a white solid, identical to the product from Example 1(c).

Method B

7β-Ammonio-7α-formamido-3-[(1,3,4-thiadiazol-2-yl)thiomethyl]ceph-3-em-4-carboxylate (75 mg, 0.2 mmol) suspended in dry dichloromethane (4 ml) was reacted with N,O/bistrimethylsilylacetamide (49 mg, 0.24 mmol) with stirring at room temperature. After 2.5 h a solution of freshly prepared D-2-(3,4-diacetoxyphenyl)-2-[(4-ethyl-2,3-dioxopiperazin-1-yl)carbonylamino]acetyl chloride (136 mg, 0.3 mmol) in dry chloromethane (1.5 ml) was added. After a further 0.5 h a solution of sodium bicarbonate (42 mg, 0.5 mmol) in water (ca. 5 ml) was added with vigorous stirring. After ca. 10 min the phases were phases were separated and the organic phase was re-extracted with water (5 ml×2). The combined aqueous extracts were washed with dichloromethane 10 ml), concentrated in vacuo, and the concentrate chromatographed on HP20SS resin eluting with acetone/water mixtures. Concentration and lyophilisation of the product containing eluant gave the tittle compound (114 mg; 70%) as an amaorphous white solid, which was identical with the product of Example 1(c).

Method C (a) To 7β-Ammonio-7α-formamido-3-[(1,3,4-thiadiazol-2-yl)thiomethyl]ceph-3-em-4-carboxylate (100 mg; 0.269 mmol) suspended in dry dichloromethane (5 ml) was added N,O-bistrimethylsilylacetamide (0.08 ml; 0.323 mmol) and chlorotrimethylsilane (0.004 ml; 0.03 mmol), and the mixture stirred at room temperature under agron to gove a clear solution.

(b) To D-2-(3,4-diacetoxyphenyl)-2-[(4-ethyl-2,3-dioxopiperazin-1-yl)carbonylamino]acetic acie (235 mg; 0.540 mmol) and trichloroethylchloroformate (0.073 ml; 0.540 mmol) in dry tetrahydrofuran (5 ml) at −10° C. under argon, was added N-methyllmorpholine (53 mg; 0.536 mmol) in tetrahydrofuran (1.24 ml) dropwise over 10 min. After 1 h, the solution prepared from part (a) was added dropwise over 20 min, the reaction warmed to 0° C. and stirred for a further 3 h. The reactio mixture was quenched with water (10 ml), and after 10 min, the pH adjusted to 6.0 with sodium bicarbonate and the title product (90 mg; 41%) isolated and purified as described in Method B.

Method D (a) To 7β-Ammonio-7α-formamido-3-](1,3,4-thiadiazol-2-yl)thiomethyl]ceph-3-em-4-carboxylate (100 mg; 0.269 mmol) suspended in dry tetrahydrofuran (5 ml) was added N,O-bistrimethylsilylacetamide (0.08 ml; 0.323 mmol) and chlorotrimethylsilane (0.004 ml; 0.03 mmol), and the mixture stirred at room temperature under argon to give a clear solution. (b) To D-2-(3,4-diacetoxyphenyl)-2-[(4-thyl-2,3-dioxopiperazin-1-yl)carbonylamino]acetic acid (174 mg; 0.4 mmol) and trichloroethylchloroformate (0.055 ml; 0.41 mmol) in dry tetrahydrofuran (5 ml) at −10° C. under argon was added 2,6-lutidine (0.047 ml; 0.41 mmol) in tetrahydrofuran (5 ml) over 10 min. After 1 h, the solution prepared in part (a) was added dropwise over 10 min, the reaceion warmed to 0° C. and stirred for a further 3 h. The reaction mixture was filtered and the filtrate diluted with water. After 30 min the pH was adjusted to 6.5, the solution concentrated as chromatography on HP20SS afforded the title product (141 mg; 65%).

Method E

To D-2-(3,4-diacetoxyphenyl)-2-[(4-ethyl-2,3-dioxopiperazin-4-yl)carbonylamino]acetic acid (176 mg; 0.404 mmol) in tetrahydrofuran (3 ml) uncer argon at −20° C. was added diphenylphosphinic chloride (0.076 ml; 0.404 mmol) in tetrahydrofuran (0.6 ml), followed by N-methylmorpholine (40 mg; 0.399 mmol) in tetrahydrofuran (1.6 ml) over several minutes. After 30 min a solution prepared as in Method D(a) was added dropwise over 20 min and the reaction warmed to 0° C. After a further 1 h, the reaction was warmed to room temperature for 3 h, quenched with water, the pH adjusted to 6.5 and concentrated. The title product was then isolated as described in Method D.

Method F

A solution of D-2-(3,4-diacetoxyphenyl)-2-[(4-ethyl-2,3-dioxopiperazin-4-yl)carbonylamino]acetic acid (303 mg; 0.697 mmol) in dry dichloromethane (6.5 ml) was treated with N-methyl-N-trimethylsilyltrifluoroacetamide (0.155 ml, 0.836 mmol) for 1h and the solution evaporated. The residue, redissolved in dry dichloromethane (6.4 ml), was treated with thionyl chloride (0.061 ml, 0.836 mmol) and after 1h this solution was evaporated. The residual white foam was dissolved in dry dichloromethane (6.3 ml) and added to a solution of 7β-ammonio-7α-formamido-3-[(1,3,4-thiadiazol-2-yl)i-thiomethyl]ceph-3-em-4-carboxylate (79 mg; 0.212 mmol) in dry dichloromethane (5ml) which had been silylated as described in Example 12, Method A. After 70 min, water (5 ml) was added and the mixture stirred vigorously. The pH was adjusted to 6.8 using saturated aqueous sodium hydrogen carbonate, the aqueous phase separated and then concentrated. The concentrate was chromagraphed as described in Method B to give the title product (72 mg; 42%).

Method G

A stirred solution of D-2-(3,4-diacetoxyphenyl-2-[(4-ethyl-2,3-dioxopiperazin-1-yl)carbonylamino]acetic acid (388 mg; 0.892 mmol) in dry tetrahydrofuran (10 ml) under argon was treated with 2,6-lutidine (0.104 ml; 0.892 mmol) in one portion. After 5 min, chlorotrimethylsilane (0.119 ml; 0.937 mmol) was added, stirring continued for a further 25 min, the reaction mixture filtered and the filtrate evaporated to give a white foam. This foam, dissolved in dry dichloromethane (10 ml), was treated with thionyl chloride (0.078 ml. 1.07 mmol) for 50 min and the mixture then evaporated. The residue was redissolved in dry dichloromethane (10 ml) and a portion (7 ml) of this solution added to a stirred solution of 7β-ammonio-7α-formamido-3-[(1,3,4-thiadiazol-2-yl)thiomethyl]ceph-3-em-j-carboxylate (93 mg; 0.249 mmol) in dry dichloromethane (5 ml) which had been presilylated as described in Method C(a). After 15 min, the reaction mixture was worked up and the title product isolated as described in Method F (125 mg; 62%).

Method H

Freshly prepared D-2-(3,4-diacetoxyphenyl)-2-[(4-ethyl-2,3-dioxopiperazin-1-yl)carbonylamino]acetyl chloride [prepared from the corresponding acid (276 mg; 0.637 mmol) according to the method described in Example 1(b)] in dry tetrahydrofuran (2.5 ml) was added to a stirred solution of 7β-ammonio-7α-formamido-3-[(1,3,4-thiadiazol-2-yl)thiomethyl]ceph-3-em-4-carboxylate (95 mg; 0.255 mmol) in dry tetrahydrofuran (5 ml) which had been presilylated according to Method D(a). After 20 min, the reaction mixture was quenched with water (7.5 ml), stirred for 10 min, the pH adjusted to 6.5 and the solution concentrated. Chromatography on HP20SS resin gave the title product (202 mg; 98%).

Method J

Dicyclohexylcarbodiimide (98 mg; 0.476 mmol) was added to a stirred solution of 7β-ammonio-7β-formamide-3-[(1,3,4-thiadiazol-2-yl)thiomethyl]ceph-3-em-4-carboxylate (148 mg; 0.397 mmol) [silylated according to Method C(a)] in dry dichloromethane (5 ml). After 5 min a solution of D-2-(3,4-diacetoxyphenyl)-2-[(4-ethyl-2,3-dioxopiperazine-1-yl)carbonylamino]acetic acid (345 mg; 0.794 mmol) in dry dichloromethane (5 ml) was added dropwise over 10 min and the resulting solution stirred for 24 h. The solid was removed by filtration and the filtrate shaken vigorously in the presence of water (15 ml). The pH was adjusted to 7.0 and the aqueous phase separated. The organic phase was re-extracted with water (10 ml) and the combined aqueous extracts concentrated. The concentrate was chromatographed on Diaion HP20SS resin to afford the title product (202 mg; 63%).

Example 11

D-2-[3,4-Bis(trimethylsilyloxy)phenyl]-2-[(4-ethyl-2,3-dioxopiperazin-1-yl)carbonylamino]acetyl chloride

Method A

A suspension of D-2-(3,4-dihydroxyphenyl)-2-[(4-ethyl-2,3-dioxopiperazin-1-yl)carbonylamino]acetic acid (176 mg, 0.5 mmol) in dry dichloromethane (6 ml), under argon, was reacted with N-methyl-N-trimethylsilyl trifluoroacetamide (3.0 mmol, 597 mg, 0.56 ml) with stirring at room temperature. After ca. 1.33 h all solids had dissolved and the mixture was evaporated at reduced pressure. The residual oil was dried on a rotary evaporator at reduced pressure and at ca. 35° C. for 0.75 h. The oil was then re-dissolved in dry dichloromethane (5 ml) and reacted with thionyl chloride (0.6 mmol, 71 mg, 0.044 ml), monitoring by infra red spectroscopy. After 1.75 h the mixture was evaporated at reduced pressure and dried in vacuo to give the product as a yellow foam (Quant.) which was used directly without further purification; νmax. (CH$_2$Cl$_2$) 3440, 1795, 1725 (sh), 1715, and 1690 cm−1.

Method B

To a suspension of D-2-(3,4-dihydroxyphenyl)-2-[(4-ethyl-2,3-dioxopiperazin-1-yl)carbonylamino]acetic acid, monohydrate (0.30 g; 0.81 mmol) in dry dichloromethane (24 ml), under argon, was added N-methyl-N-trimethylsilyltrifluoroacetamide (1.28 ml; 1.376 g; 6.90 mmol) and trimethylchlorosilane (0.09 ml; 0.077 g; 0.71 mmol). The mixture was stirred at room temperature for ca. 60 h. The solution was evaporated at reduced pressure and the residual oil dried at reduced pressure at ca. 35° C. for 0.5 h followed by 0.5 h at room temperature. The oil was redissolved in dry dichloromethane (15 ml) and reacted with thionyl chloride (0.075 ml; 0.122 g; 1.03 mmol) at room temperature, monitoring by infra red spectroscopy. After ca. 4 h the solution was evaporated at reduced pressure to give the product as a yellow solid (Quant.) which was dried at reduced pressure for 0.25 h and used directly without further purification.

Method C

D-2-(3,4-Dihydroxyphenyl)-2-[(4-ethyl-2,3-dioxopiperazin-1-yl)carbonylamino]acetic acid, monohydrate (0.30 g; 0.81 mmol) was reacted with N,O-bistrimethylsilyltrifluoroacetamide (0.90 ml; 0.877 g; 3.41 mmol) and trimethylchlorosilane (0.09 ml; 0.077 g; 0.71 mmol) followed by thionyl chloride (0.075 ml; 0.122 g; 1.03 mmol) as in Example 11, Method B, to give the product (Quant.) which was used directly without further purificaiton.

Example 12

Sodium 7β-[D-2-(3,4-Dihydroxyphenyl)-2-[(4-ethyl-2,3-dioxopiperazin-1-yl)carbonylamino]acetamido]-7α-formamdio-3-[(1,3,4-thiadiazol-2-yl)thiomethyl]ceph-3-em-4-carboxylate

Method A

A suspension of 7β-ammonio-7α-formamido-3-[(1,3,4-thiadiazol-2yl)thiomethyl]ceph-3-em-4-carboxylate (0.760 g, 2.04 mmol) in dry dichloromethane (40 ml) was reacted with N,O-bistrimethylsilylacetamide (0.498 g, 2.45 mmol) at room temperature with vigorous stirring. Further portions of N,O-bistrimethylsilylacetamide (0.1 ml, 0.83 g, 0.4 mmol) were added after 2.75 h and 3.7 h. After 4.5 h the mixture was cooled to 0° C. and a solution of D-2-[3,4-bis(trimethylsilyloxy)-phenyl]-2-[(4-ethyl-2,3-dioxopiperazine-1-yl)carbonylamino]acetyl chloride (freshly prepared from the corresponding carboxylic acid (1.074 g, 3.06 mmol) as in Example 11, Method A) in dry dichloromethane (15 ml) was added dropwise with stirring. After 0.5 h a further portion of the above acid chloride (0.358 g, 1.02 mmol) in dry dichloromethane (5 ml) was added dropwise with stirring.

After a further 0.5 h, a solution of sodium hydrogen carbonate (0.514 g, 6.12 mmol) in water (ca. 50 ml) was added with vigorous stirring at room temperature and the pH of the mixture was ca. 6.5. The phases were separated and the organic phase carefully extracted with further portions of water (3×50 ml). The combined aqueous extracts, after the additioin of acetone, were concentrated at reduced pressure to ca. 30 ml. The concentrate was chromatographed on HP20SS resin (ca. 150 ml) eluting with water (500 ml), 2%, 3%, 4%, 5% acetone/water (500 ml each). The product containing fractions were concentrated at reduced pressure and the concentrate lyophilized to give the product (0.756 g, 51%) as an emorphous white solid.

Method B

To a suspension of 7β-ammonio-7α-formamido-3-[(1,3,4-thiadiazol-2-yl)thiomethyl]ceph-3-em-4-carboxylate (160 mg; 0.43 mmol) in dry dichloromethane (10 ml) at room temperature under argon was added N,O-bistrimethylsilylacetamide (0.128 ml; 105 mg; 0.516 mmol) and trimethylchlorosilane (12 μl; 10 mg; 0.095 mmol). The mixture was stirred until a clear solution was obtained (ca. 2h), then cooled to 0° C. and a solution of D-2-[3,4bis(trimethylsilyloxy)phenyl[-2-[(4-ethyl-2,3-dioxopiperazin-1-yl)carbonylamino]acetyl chloride (½ the product from Example 11, Method B) in dry dichloromethane (5 ml) added over 5 min. After stirring for 1 h the solvent was evaporated off at reduced pressure, the residue dissolved in a mixture of tetrahydrofuran (7.5 ml) and water (2.5 ml), and the solution stirred at room temperature for 20 min. The pH was then adjusted to 6.5 by the addition of aqueous sodium bicaronate solution, the mixture diluted with water (5 ml), then concentrated at reduced pressure to remove tetrahydrofuran. The concentrate was chromatographed on 'Diaion' HP20SS resin as in Example 12, Method A top give the product (198 mg; 63%).

Method C

To a suspension of 7β-ammonio-7α-formamido-3-[(1,3,4-thiadiazol-2-yl)thiomethyl]ceph-3-em-4-carboxylate (320 mg; 0.86 mmol) in dry dichloromethane at room temperature under argon was added N,O-bis-trimethylsilyl acetamide (0.29 ml; 237 mg; 1.16 mmol) and trimethylchlorosilane (24 μl; 20 mg; 0.19 mmol). The mixture was stirred until a clear solution was obtained (ca. 1.75 h), then cooled to 0° C. and a solution of D-2-[3,4-bis(trimethylsilyloxy)phenyl)]-2-[(4-ethyl-2,3-dioxopiperazin-1-yl)carbonylamino]acetyl chloride (the product of Example 11, Method C) in dry dichloromethane (10 ml) was added over 10 min. After stirring at 0° C. for 1 h, isolation and purification as in Example 12, Method B gave the product (333 mg; 54%).

Method D

To a suspension of 7β-ammonio-7α-formamido-3-[(1,3,4-thiadiazol-2-yl)thiomethyl]ceph-3-em-4-carboxylate (112 mg; 0.3 mmol) in dry tetrahydrofuran (8 ml) at room temperatrure under argon was added N,O-bistrimethylsilyl trifluoroacetamide (0.096 ml, 93 mg, 0.36 mmol) and trimethylchlorosilane (10 μl; 9 mg; 0.08 mmol). The mixture was stirred at room temperature for 2 h to give a clear solution, to which (after storage at ca. 4° C. for 18 h) was added a solutin of D-2-[3,4-bis(trimethylsilyloxy)phenyl]-2[(4-ethyl-2,3-dioxopiperazin-1yl)carbonylamino]acetyl chloride (0.3 mmol, prepared via the method of Example 11, Method B) in dry tetrahydrofuran (5 ml) at 0° C. over 15 min. The resulting solution was stirred at 0° C. for 2.25 h, then water (ca. 3 ml) added and stirring continued at room temperature for 15 min. The pH was adjusted to 6.5 by the addition of dilute aqueous sodium hydroxide solution and the resulting solution concentrated to remove tetrahydrofuran. Purification of the concentrate as in Example 12, Method A gave the product (114 mg; 52%).

Method E

To D-2-(3,4-dihydroxyphenyl)-2-[(4-ethyl-2,3-dioxopiperazin-1-yl)carbonylamino]acetic (100 mg; 0.271 mmol) suspended in dichloromethane (5 ml) under argon was added N,O-bis(trimethylsilyl)carbamate (138 mg; 0.673 mmol) and the mixture refluxed for 5.5 h. The resulting solution was stirred at room temperature overnight, purged with argon and thionyl chloride (3.326 ml; 0.365 mmol) added. After stirring for a further 2.5 h the solution was purged again with argon and then added dropwise to a stirred solution of 7β-ammonio-7α-formamido-3-[(1,3,4-thiadiazol-2-yl)thiomethyl]ceph-3-em-4-carboxylate (100 mg; 0.269 mmol) in dichloromethane (5 ml) which had been presilylated as described in Method B. After 4 h the title product (91 mg; 47%) was isolated and purified as described in Method B.

Method F

Dicyclohexylcarbodiimide (119 mg; 0.576 mmole) was added to a stirred solution of 7β-ammonio-7α-formamido-3-[(1,3,4-thiadiazol-2-yl)thiomethyl]ceph-3-em-4-carboxylate (179 mg; 0.480 mmol), which had been silylatd in dry tetrahydrofuran (5 ml) according to Example 10, Method D(a). After 5 min, a solution of D-2-(dihydroxyphenyl)-2[(4-ethyl-2,3-dioxopiperazin-1-yl) carbonylamino]acetic acid (337 mg; 0.96 mmol) in dry tetrahydrofuran (1.5 ml) was added and the resulting mixture stirred for 24 h. Water (10 ml) was added, pH adjusted to 6.0 and the mixture stirred vigorously for 10 min. After filtration to remove insoluble materials, the mixture was concentrated and the concentrate chromatographed on Diaion HP20SS resin to give the title product (96 mg; 27.5%).

Method G (a) D-2-(3,4-Dihydroxyphenyl)-2[(4-ethyl-2,3-dioxopiperazin-1-yl)carbonylamino]acetic acid monohydrate (1.85 g; 0.005 mol) was dissolved in tetrahydrofuran (30 ml) and treated at ambient temperature with excesses of chlorotrimethlsilane (7 ml) and hexamethyldisilazane (8 ml) for 1 h. The solvent was removed in vacuo and the residue redissolved in toluene (50 ml). The insoluble material was removed by filtration and the filtrate re-evaporated to a cloudy oil. The oil was azeotroped with a further portion of toluene (50 ml). This oil was redissolved in dichloromethane (400 ml) and treated with excess thionyl chloride (20 ml). The solution was stirred at ambient temperature for 1 h and the solvent removed in vacuo at 10°–15°. The residue was azeotroped with further dichloromethane (2×50 ml) to give a foam which was redissolved in tetrahydrofuran (60 ml) and used immediately for the next stage.

(b) Meanwhile 7β-ammonio-7α-formamido-3-[(1,3,4-thiadiazol-2-yl)thiomethyl]ceph-3-em-4-carboxylate (1.44 g; 0.00388 mol) was suspended at ambient temperature in tetrahydrofuran (60 ml) containing N,O-bis-trimethylsilylacetamide (1.8 ml) and chlorotrimethylsilane (1 drop). The clear solution obtained in 5 min, was stirred for 1 h and then cooled to −20° C. The acid chloride solution from (a) was added over a period of 10 min and the solution then allowed to attain ambient temperature and stirred for a further 1 h. Water (50 ml) was added and the solution stirred for 1 h. The pH was adjusted to 6.5 with 1 molar sodium bicarbonate solution and the mixture washed with toluene (2×50 ml). Residual toluene was removed from the aqueous solution by evaporation and the pH reduced to 1.5–2.0 with 2 molar hydrochloric acid. The precipitated acid product was removed by filtration and dried to give (1.9 g; 69%) buff coloured material. Purification of the title sodium salt (obtained by dissolution in aqueous sodium bicarbonate at pH 7.0) could be achieved by chromatography on HP20SS eluting with water follow by 5% acetone/water.

Method H

7β-Ammonio-7α-formamido-3-[(1,3,4-thiadiazol-2-yl) thiomethyl]ceph-3-em-4-carboxylate (162 mg; 0.434 mmol) was dissolved in water (5 ml) at pH 5.6 and 1-(3-dimethylaminopropyl)-3-ethylcarbodiimide hydrochloride (100 mg; 0.521 mmol) added, followed by D-2-(3,4-dihydroxyphenyl)-2-[(4-ethyl-2,3-dioxopiperazin-1-yl)carbonylamino]acetic acid (320 mg; 0.868 mmol). The pH was adjusted and the reaction mixture stirred at room temperature to give the title product.

Example 13

7β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic Acid (a) D-2-(3,4-Dihydroxyphenyl)-2-[(4-ethyl-2,3-dioxopiperazin-1-yl)carbonylamino]acetic acid (0.9 g; 0.0025 mol) was dissolved in tetrahydrofuran (20 ml) and excess thionyl chloride (10 ml) added. The solution was stirred at 20° C. for 1 h. The solvent was removed in vacuo and the foam azeotroped with dichloromethane (2×50 ml). The yellow foam was re-dissolved in tetrahydrofuran (20 ml) and used immediately for the next stage.

(b) 7β-Ammonio-7α-formamido-3-[(1,3,4-thiadiazol-2-yl) thiomethyl]ceph-3-em-4-carboxylate (! 0.72 g; 0.00194 mol) was suspended in tetrahydrofuran (30 ml) at 20° C., and N,O-bistrimethylsilylacetamide (0.9 ml; 0.0036 mol) was added followed by 1 drop of chlorotrimethylsilane. After 10 min the resulting solution was cooled to −20° C. and the acid chloride from part (a) was added dropwise over 10 min. When the addition was complete the reaction mixture was allowed to attain ambient temperature and stirred for a further 1 h. Water (20 ml) was added, the solution stirred for another 1 h and the pH adjusted to 6.5 by addition of 1 molar sodium bicarbonate. The mixture was washed with toluene (2×50 ml), the aqueous phase separated and residual toluene was removed in vacuo at 30° C. The pH of the aqueous solution was adjustd to 2.0 by addition of 2M-hydrochloric acid. The precipitated title product was filtered off and dried in vacuo (0.42 g; 31%). Further purification could be achieved by re-acidification of a solution of the sodium salt at pH 6.5 (sodium bicarbonate) to pH 2.0 with 2M-hydfrochloric acid; δH [(CD$_3$)$_2$SO] (major rotamer only) 1.07 (3H, t, J 7 Hz), 3.2–3.7 (6H, complex m), 3.8–4.0 (2H, m), 4.20 and 4.58 (2H, ABq, J 13.3 Hz), 5.12 (1H, s), 5.50 (1H, d, J 7.9 Hz), 6.6–6.9 (3H, m), 8.03 (1H, d, J 0.9 Hz), 8.7–9.1 (2H, br s, exch), 9.38 (1H, s, exch), 9.55 (1H, s), 9.73 (1H, d, J 7.9 Hz), (signals from 9.38–9.8 obscure 1H, s), and 12.5–14.5 (1H, br s, exch).

Example 14

Pivoloyloxymethyl 7β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph3-em-4-carboxylate Pivaloyloxymethyl bromide (68 mg, 0.348 mmol) in acetone (1 ml) was added to a stirred solution of sodium iodide (55 mg, 0.365 mmol) in acetone (1 ml). After 5 min the solution was filtered and the residue washed with acetone (1 ml). A portion of the filtrate (2.25 ml) was added to a stirred solution of sodium 7β-[D-2-(3,4-dihydroxyphrenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylate (127 mg, ! 0.174 mmol) in dry N,N-dimethylrformamide (2 ml). After 5 min ethyl acetate (25 ml) was added and the mixture washed with water (5×20 ml). The organic phase was dried (MgSO$_4$) then filtered and the filtrate evaporated at reduced pressure. The resulting solid was triturated with anhyd. diethyl ether, filtered off and washed with more ether before drying in vacuo, to afford the title compound (64 mg, 45%); λ$_{max}$ (EtOH) 270 nm (ε$_m$ 15874); νmax (CH$_2$Cl$_2$)3270, 1785, 1750, 1710, and 1685 cm−1; δ$_H$ [(CD$_3$)$_2$CO](major rotamer) 1.10–1.25 (12H, m), 3.41 and 3.60 (2H, ABq, J 17.0 Hz), 3.50 (2H, q, J 7.2 Hz), 3.64–3.75 (2H, m), 3.95–4.10 (2H, m), 4.26 and 4.74 (2H, ABq, J 13.6 Hz), 5.20 (1H, s), 5,52 (1H, d, J 7.0 Hz), 5.85 and 5.99 (2H, ABq, J 5.6 Hz), 6.70–7.05 (3H, m), 7.90 (1H, s, exch. D$_2$O), 8.07 (1H, s, exch. D$_2$O), 8.18 (1H, d, J 1.0 Hz), 8.44 (1H, s, exch. D$_2$O), 8.53 (1H, s, exch. D$_2$O), 9.41 (1H, s), and 9.84 (1h, d, J 4.0 Hz); [FAB (+ve ion) (thioglycerol) MH+ 821].

Example 15

Sodium 7β-[D,L-2-(4-Aminophenyl)-2-[(4-ethyl-2.3-dioxopiperazin-1-yl)carbonylamino]acetamido]-7α-formamido-3-[(1,3,4-thiadiazol-2-yl)thiomethyl]ceph-3-em-4-carboxylate (a)

D,L-2-[(4-Ethyl-2,3-dioxopiperazin-1-yl)carbonylamino]-2-[4-(4-nitrobenzyloxycarbonyl)amino]phenyl acetic acid (4-Nitrobenzyloxycarbonyl)aniline (1.36 g; 5 mmol) and D,L-2-[(4-ethyl-2,3-dioxopiperazin-1-yl)carbonylamino]-2-hydroxyacetic acid (1.36 g; 5.25 mmol) were added consecutively to a mixture of acetic acid (2.5 ml) and concentrated sulphuric acid (2.5 ml). The mixture was vigorously stirred at ambient temperature for 1h, then poured onto ice-water and extracted with ethyl acetate (2×25 ml). The total organic extract was washed once with saturated brine, dried over magnesium sulphate and evaporated to dryness (ca. 2.5 g). Trituration with a little ethyl acetate followed by seeding afforded the product acid (3.58 g); evaporation of the mother liquors followed by chromatography on silica gel afforded further equally pure product (total yield 0.89 g, 35%); ν$_{max}$. (KBr) 1711 (vs), 1678, 1606 (m), 1520, and1347 cm−1; δ[(CD$_3$)$_2$CO]1.17 (3H, t, J 7 Hz), 3.51 (2H, q, J 7 Hz),3.71 and 4.06 (4H, 2 m), 5.35 (2H, s), 5.45 ! 1H, d, J 6.5 Hz), 7.42 and ! 7.62 (4H, dd), 7.22 and 8.27 (4H, dd), 9.07 (1H, br s, D$_2$O exchanged), 9.90 (1H, d, J 6.5 Hz, D$_2$O exchanged); [MH+ 514 (FAB +ve ion, thioglycerol)].

(b) Diphenylmethyl 7β-[D,L-2-[(4-Ethyl-2,3-dioxopiperazin-1yl)carbonylamino]-2[4-(4-nitrobenzyloxycarbonyl)amino]phenylacetamido]-7α-formamido-3-[(1,3,4-thiadiazol-2-yl)thiomethyl]ceph-3-em-4-carboxylate To a solution of D,L-2-[(4-ethyl-2,3-dioxopiperazin-1-yl)-carbonylamino]-2-[4-(4nitrobenzyloxycarbonyl)-amino]phenyl acetic acid (172 mg; 0.336 mmol) in dry N,N-dimethylformamide (1 ml) and dry tetrahydrofuran (3 ml) was added, with stirring, a solution of dicyclohexylcarbodiimide (76 mg; 0.369 mmol) and diphenylmethyl 7β-amino-7α-formamido-3[(1,3,4-thiadiazol-2-yl)thiomethyl]ceph-3-em-4-carboxylate (181 mg;

0.336 mmol) in dry tetrahydrofuran (3 ml). After 16 h, the solid was removed by filtration and the filtrate concentrated to give a yellow syrup which was partitioned between ethyl acetate and 10% saturated aqueous sodium bicarbonate. The separated organic phase was wahsed with 0.1M-hydrochloric acid, saturated brine (4x), dried (MgSO$_4$), evaporated and the residue chromatographed on silica gel to give the title product as a cream coloured solid (186 mg; 54%); $\nu_{max}$.(Nujol) 3250, 1780, 1730, 1710 1675 , and 1605 cm$^{-1}$; δ[(CD$_3$)$_2$CO; major rotamer only]1.16 (3H, t, J 7.4 Hz), 3.19 and 3.36 (2H, ABq, J 16 Hz), 3.50 (2H, q, J 7.4 Hz), 3.6–3.8 and 3.9–4.1 (each 2H, m), [(4.36 and 4.65) and (4.37 and 4.70), together 2H, J 13.6 and 13.5 Hz respectively, each ABq], 5.30 (1H, s), 5.35 (2H, br s), 5.68 and 5.73 (together 1H, each d, J 6.8 and 7.0 Hz respectively), 6.98 (1H, s), 7.2–7.8 (together 16H, m), 8.2–8.3 (together 3H, m), 8.53, 8.56, 8.71 and 9.04 (together 3H, each br s), 9.29 and 9.30 (together 1H, each s), and 10.00 (1H, br d, J 7 Hz). (Addition of D$_2$O caused the signals at 8.53, 8.56, 8.71, 9.04 and 10.00 to disappear whilst those centered at 5.68 and 5.73 collapsed to 2×s); [FAB (+ve ion) (thioglycerol) MH+ 1035].

(c) Sodium 7β-[D,L-2-[(4-Ethyl-2,3-dioxopiperazin-1-yl)carbonylamino[-2-[4-(4-nitrobenzyloxycarbonyl)amino]-phenylacetamido]-7α-formamido-3-[(1,3,4-thiadiazol-2-yl)thiomethyl]ceph-3-em-4-carboxylate A solution of diphenylmethyl 7β-[D,L-2-[(4-ethyl-2,3-dioxo-piperazin-1-yl)carbonylamino]-2-[4-(4-nitrobenzyloxycarbonyl)amino]-phenylacetamido]-7α-formamido-3-[(1,3,4-thiadiazol-2-yl)thiomethyl]ceph-3-em-4-carboxylate (34 mg; 0.033 mmol) and anisole (107 mg; 0.98 mmol) in dichloromethane (2 ml) at ice bath temperature was treated with trifluoroacetic acid (112 mg; 0.986 mmol). After 30 min, the solution was evaporated to dryness and the residue triturated with dry ether to give a white solid which was suspended in water and the pH adjusted to 6.6 with diluted sodium hydrogen carbonate. Chromatography on Diaion HP20SS and lyophilisation of the product-containing fractions gave the title compound (16 mg; 55%); $\nu_{max}$. (Nujol) 3200, 1760, 1710, 1670, and 1600 cm$^{-1}$; δ[D$_2$O/(CD$_3$)$_2$CO; major rotamer only] 1.22 (3H, t, J 7.2 Hz), 3.11 and 3.18 (together 1H, each d, J 16.6 Hz), 3.45–3.6 (together 3H, m), 3.65–3.85 (together 2h, m) 4.0–4.2 (together 3H, m), 4.22 and 4.27 )together 1H, each d, J 14 hz), 5.21 and 5.28 (together 1H, each s), 5.37 (2H, br s), 5.59 and 5.64 (1H, each s), 7.4–7.6 (4H, m), 7.7–7.8 and 8.25–8.35 (together 4H, m), 8.15 and 8.18 (together 1H, each s), 9.43 and 9.46 (together 1H, each s).

(d) Sodium 7β-[D,L-2-(4-Aminophenyl-2-[(4-ethyl-2,3-dioxopiperazin-1-yl)carbonylamino]acetamido]-7α-formamido-3-](1,3,4-thiadiazol-2-yl)thiomethyl]-ceph-3-em-4-carboxylate A solution of sodium 7β-[D,L-2[(4-ethyl-2,3-dioxopiperazin-1-yl)carbonylamino]-2-[4-(4-nitrobenzyloxycarbonyl)amino]phenylacetamido]-7α-formamido-3-[(1,3,4-thiadiazol-2-yl)thiomethyl]ceph-3-em-4-carboxylate (39 mg; 0.044 mmol) in water (4 ml) and tetrahydrofuran (3 ml) was hydrogenolysed for 20 min in the presence of 10% palladium on charcoal (70 mg). After After filtration to remove catalyst, the filtrate was concentrated and the concentrate chromatographed on Diaion HP20SS resin. The product-containing fractions were combined and then lyophilised to give the title compound (20 ml; 67%); $\nu_{max}$. (H$_2$O) 232 (ε 18520) and 248 nm (18850); $\nu_{max}$.(KBr) 3379, 2975, 1767, 1709, 1677, and 1609 cm$^{-1}$; δ (D$_2$O; major rotamer only) 1.17 (3H, t, J 1.4 Hz), 3.04 and 3.05 (together 1H, each d, J 17.0 and 16.9 hz respectively), 3.4–3.6 (together 3H, m), 3.6–3.75 (together 2H, m), 3.9–4.1 (together 3H, m), 4.39 and 4.48 (together 1H, each d, J 13.8 and 13.9 Hz respectively), 5.15 and 5.26 (together 1H, each s), 5.36 and 5.40 (together 1h, each s), 6.8–6.9 and 7.3–7.5 (together 4H, m), 8.07 and 8.10 (together 1H, each s), and 9.37 and 9.39 )together 1H, each s).

Example 16

7β-[D-2-(3,4-Diacetoxyphenyl)-2-[(4-ethyl-2,3-doixopiperazin-1-yl)carbonylamino]acetamido]-! 7α-formamido-3-[(1,3,4-thiadiazol-2-yl)thiomethyl]ceph-3-em-4-carboxylic Acid Sodium 7β-[D-! 2-(3,4-diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4carboxylate (106 mg; 0.131 mmol) was dissolved in water (3 ml) and the pH adjusted to 2.4 with 5M-hydrochloric acid. The precipitate was filtered off and dried in vacuo to give the title product (81 mg; 78%) as a white solid; δ$_H$[(CD$_3$)$_2$CO; major rotamer]1.17 (3H, t, J 7.2 Hz), 2.25 (6H, s), 3.21 and 3.44 (2H, ABq, J 16 Hz), 3.49 (2H, q, J 7.2 Hz), 3.6–3.75 (2H, m), 3.95–4.1 (2H, m), 4.33 and 4.77 (2H, ABq, J 13 Hz), 5.22 (1H, s), 5.77 (1H, d, J 6.9 Hz), 7.2–7.5 (3H, m), 8.19 9.41 (1H, s), and 10.06 (1H, d, H 6.9 Hz). The acrboxylic acid OH signal was not clearly discernible.

Example 17

Minimum Inhibitory Concentration (MIC) values of compounds of the invention against *P. mirabilis* C977, *S. marcescens* US 32, and *P. aeruginosa* K79961 were determined by serial dilution in Iso-Sensitest Agar (from Oxiod Ltd., Basinstoke, England). The plates were inoculated with 10$_4$ colony forming units and incubated overnight at 37° C. The MIC values recorded in Table 1 were the lowest concentration of antibiotic to inhibit growth. Comparative data for sodium 7β[2-(3,4-diacetoxyphenyl)-2-[(4-ethyl-2,3-dioxopiperazin-1yl)carbonylamino]acetomido]-7α-formamido-3-[(2-methyl-1,3,4-thiadiazol-5yl)thiomethyl]ceph-3em-4-carboxylate (Compound A), disclosed in European Patent Application No. 82303821.1 (Publication No. 0 071 395) are also given.

MIC data
TABLE 1

| Organism | MIC (μg/ml) | | |
|---|---|---|---|
| | Example 1 | Example 2 | Compound A |
| *Proteus mirabilis* C977 | 1.0 | 1.0 | 4.0 |
| *Serratia marcescens* US 32 | 0.25 | 0.12 | 1.0 |
| *Pseudomonas aeruginosa* K79961 | 0.25 | 0.5 | 2.0 |

We claim:
1. A compound selected from the group consisting of

7β-[D-2-(3,4-Diacetoxypenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid;

[(1,3,4-thiadiazol-2-yl)thiomethyl]ceph-3-em-4-, and pharmaceutically acceptable salts thereof and in vivo hydrolyzable esters thereof.

2. The compound according to claim 1 which is 7-β--[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carbixylic acid, a pharmaceutically acceptable salt thereof or an in vivo hydrolyzable ester thereof.

3. A pharmaceutical composition useful for treating bacterial infections in humans and domestic mammals which comprises an antibacterially effective amount of a compound selected from the group consisting of 7β--[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; 7-β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; pharmaceutically acceptable salts thereof and in vivo hydrolyzable esters thereof, in combination of a pharmaceutically acceptable carrier.

4. A composition according to claim 3 wherein the compound is 7-β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2yl)thiomethyl]ceph-3-em-4-carboxylic acid, a pharmaceutically acceptable salt thereof or an in vivo hydrolyzable ester thereof.

5. A method of treating bacterial infections in humans and domestic mammals which comprises administering to a human or domestic in need thereof an antibacterially effective amount of a compound selected from the group consisting of 7β-[D-2-(3,4-Diacetoxyphenyl)2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; 7-β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; pharmaceutically acceptable salts thereof and in vivo hydrolyzable esters thereof, in combination with a pharmaceutically acceptable carrier.

6. A method according to claim 5 wherein the compound is 7-β-[D-2-(3,4-Dihydroxoyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid, a pharmaceutically acceptable salt thereof or an in vivo hydrolyzable ester thereof.

7. A pharmaceutical composition useful for treating bacterial infections in humans and domestic mammals which comprises an antibacterially effective amount of a compound selected from the group consisting of 7β--[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; 7-β-[D-2-(3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; pharmaceutically acceptable salts thereof and in vivo hydrolyzable esters thereof, and a betalactamase inhibitory amount of a betalactamase inhibitor, in combination with a pharmaceutically acceptable carrier.

8. A composition according to claim 7 wherein the compound is 7-β-[D-2-(3,4-Dihydroxyphenyl)-1-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid, a pharmaceutically acceptable salt thereof or an in vivo hydrolyzable esters thereof.

9. A method of treating bacterial infections in humans and domestic mammals which comprises administering to a human or domestic mammal in need thereof an antibacterially effective amount of a compound selected from the group consisting of 7β-[D-2-(3,4-Diacetoxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; 7-β-[D-2-(qb 3,4-Dihydroxyphenyl)-2-[(4-ethyl-2,3-dioxopiperazin-1-yl)carbonylamino]acetamido]-7α-formamido-3-[(1,3,4-thiadiazol-2-yl)thiomethyl]ceph-3-em-4-carboxylic acid; pharmaceutically acceptable salts thereof and in vivo hydrolyzable esters thereof, and a betalactamase inhibitory amount of a betalactamase inhibitor, in combination with a pharmaceutically acceptable carrier.

10. A method according to claim 9 wherein the compound is 7-β-[D-2-(3,4-Dihydroxyphenyl)-2-[(4ethyl-2,3-dioxopiperazin-1-yl)carbonylamino]acetamino]-7α-formamido-3-[(1,3,4-thiadiazol-2-yl)thiomethyl]ceph-3-em-4-carboxylic acid, a pharmaceutically acceptable salt thereof or an in vivo hydrolyzable ester thereof.

* * * * *